US010304568B2

(12) United States Patent
Melkonyan

(10) Patent No.: US 10,304,568 B2
(45) Date of Patent: May 28, 2019

(54) DECOMPOSITION OF NON-STATIONARY SIGNALS INTO FUNCTIONAL COMPONENTS

(71) Applicant: KAOSKEY PTY LIMITED, Thornleigh (AU)

(72) Inventor: Dmitri Melkonyan, Sydney (AU)

(73) Assignee: KAOSKEY Pty Ltd., Thornleigh, New South Wales (AU)

( * ) Notice: Subject to any disclaimer, the term of this patent is extended or adjusted under 35 U.S.C. 154(b) by 206 days.

(21) Appl. No.: 15/029,301

(22) PCT Filed: Oct. 13, 2014

(86) PCT No.: PCT/AU2014/050283
§ 371 (c)(1),
(2) Date: Apr. 14, 2016

(87) PCT Pub. No.: WO2015/054744
PCT Pub. Date: Apr. 23, 2015

(65) Prior Publication Data
US 2016/0224757 A1  Aug. 4, 2016

(30) Foreign Application Priority Data
Oct. 14, 2013  (AU) ................................ 2013903948

(51) Int. Cl.
*A61B 5/00* (2006.01)
*A61B 5/04* (2006.01)
(Continued)

(52) U.S. Cl.
CPC ............... *G16H 50/50* (2018.01); *A61B 5/04* (2013.01); *A61B 5/7246* (2013.01);
(Continued)

(58) Field of Classification Search
CPC ..... G16H 50/50; G06F 19/3437; G06F 17/11; G06F 17/14; G01R 23/167; G06K 9/0055;
(Continued)

(56) References Cited

U.S. PATENT DOCUMENTS
6,381,559 B1  4/2002 Huang

OTHER PUBLICATIONS

Melkonian et al., "Chaotic Dynamics of ECG Waveforms at Global and Microscopic Scales: Theory and Applications," Open Cybernetics & Systemics Journal, 2001, vol. 5, pp. 32-44 (online journal), retrieved from Internet on Apr. 12, 2014.*
(Continued)

*Primary Examiner* — Saif A Alhija
(74) *Attorney, Agent, or Firm* — Cooper & Dunham LLP

(57) ABSTRACT

A method of signal processing and, in particular, a method of decomposing non-stationary signals representative of a physiological phenomenon into functional components, and to estimate parameters characterizing each of those functional components. The method utilises means for estimating dynamic and baseline trends in the time course of the signal, means for dividing the non-stationary signal into the segments over which the functional components are developed and means for compensating for overlap from QGK matched to preceding functional components to form an ECK. The compensation comprises means for transforming the ECK to a frequency domain, means for estimating the weight and dispersion parameters of the QGK, and validation of the parameter reliability, means for estimating the onset time of the QGK, means for expansion of the model of the non-stationary signal after each cycle of recursion, means for removal of unfavourable QGKs and rearrangement of remaining QGKs and means for creating partial models of the non-stationary signal with parameters belonging to predefined classes.

8 Claims, 15 Drawing Sheets

(51) Int. Cl.
*G06K 9/00* (2006.01)
*G06F 17/11* (2006.01)
*G06F 17/14* (2006.01)
*G16H 50/50* (2018.01)
*G01R 23/167* (2006.01)
*G06F 19/00* (2018.01)

(52) U.S. Cl.
CPC .......... *A61B 5/7253* (2013.01); *A61B 5/7264* (2013.01); *G01R 23/167* (2013.01); *G06F 17/11* (2013.01); *G06F 17/14* (2013.01); *G06F 19/00* (2013.01); *G06K 9/0055* (2013.01)

(58) Field of Classification Search
CPC ... A61B 5/7264; A61B 5/7246; A61B 5/7253; A61B 5/04
USPC .......................................................... 703/2
See application file for complete search history.

(56) References Cited

OTHER PUBLICATIONS

Melkonian et al., "High-Resolution Fragmentary Decomposition—A Model-Based Method of Non-Stationary Electrophysiological Signal Analysis," Journal of Neuroscience Methods, 2003, vol. 131, No. 1, pp. 149-159.*

D. Melkonian et al., "Chaotic Dynamics of ECG Waveforms at Global and Microscopic scales: theory and applications", The Open Cybernetics and Systemics Journal, vol. 5, No. 1, May 24, 2011, 13 pages.

A. Effern et al., "Nonlinear denoising of transient signals with application to event-related potentials", Physica D, vol. 140, No. 3-4, Jun. 1, 2000, 10 pages.

H. Georg Schulze et al., "Fully automated High-Performance Signal-to-Noise Ratio Enhancement Based on an Iterative Three-Point Zero-Order Savitzky-Golay Filter", Applied Spectroscopy, vol. 62, No. 10, Oct. 1, 2008, 7 pages.

D. Melkonian et al., "Dynamics of the Eyeblink EMG at Global and Microscopic Scales", retrieved May 15, 2017 from https://www.researchgate.net/profile/Dmitriy_Melkonian, 13 pages.

International Search Report and Written Opinion dated Jan. 5, 2015, in connection with International Patent Application No. PCT/AU2014/050283, 9 pgs.

Melkonian et al., "Numerical Fourier Transform Spectroscopy of EMG Half-Waves: Fragmentary-Decomposition-Based Approach to Nonstationary Signal Analysis," Biological Cybernetics, 1999, vol. 81, No. 5-6, pp. 457-467.

* cited by examiner

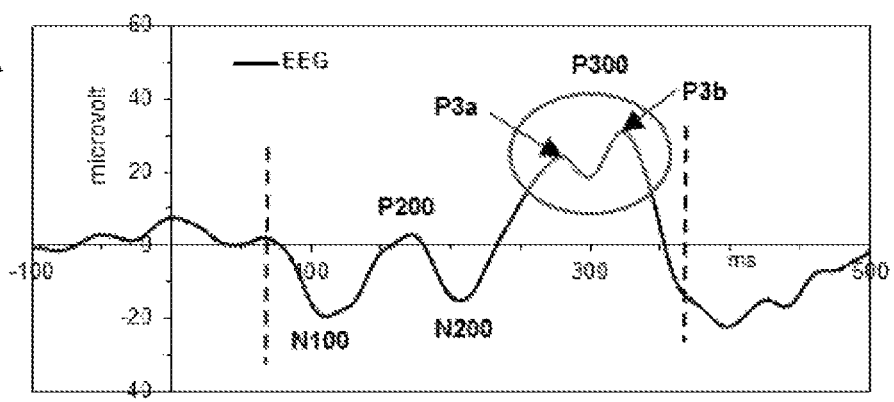
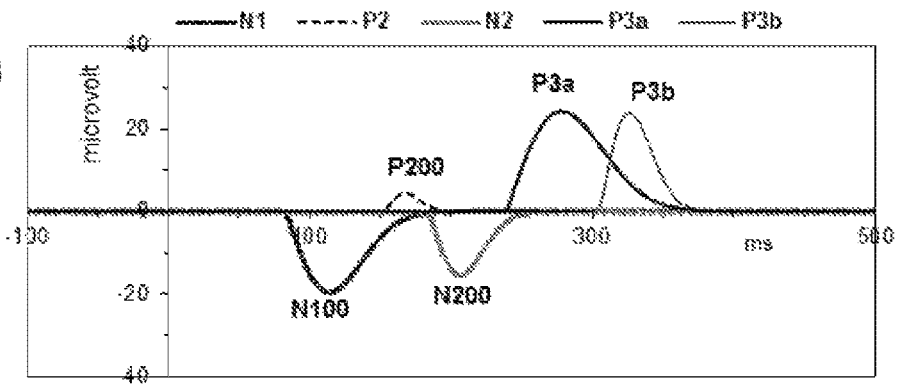
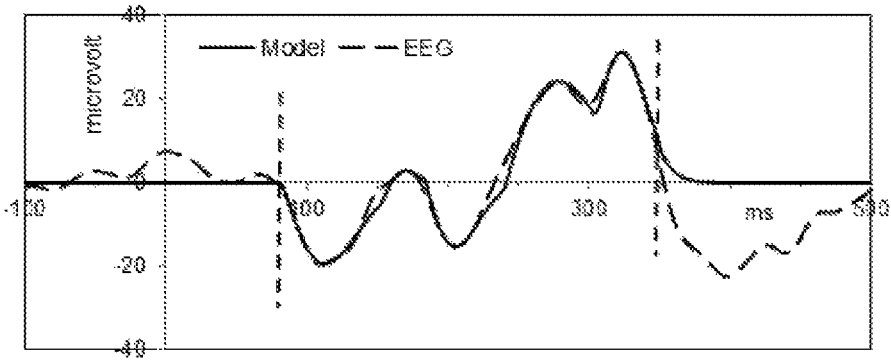

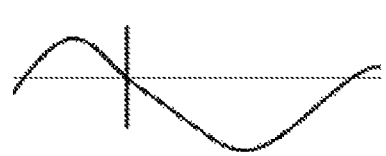
FIG. 5A
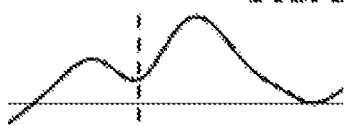
FIG. 5B
FIG. 5C
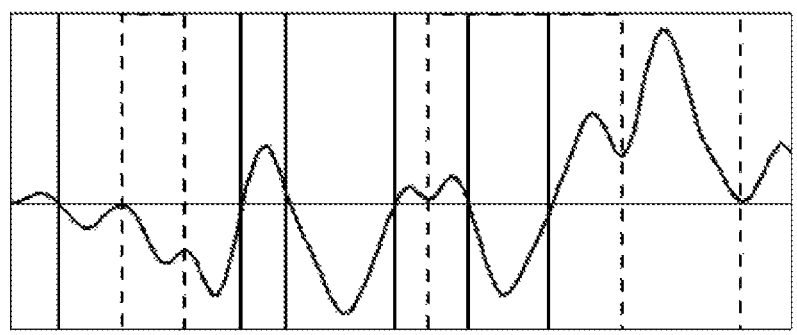

High resolution segmentation
FIG. 6A
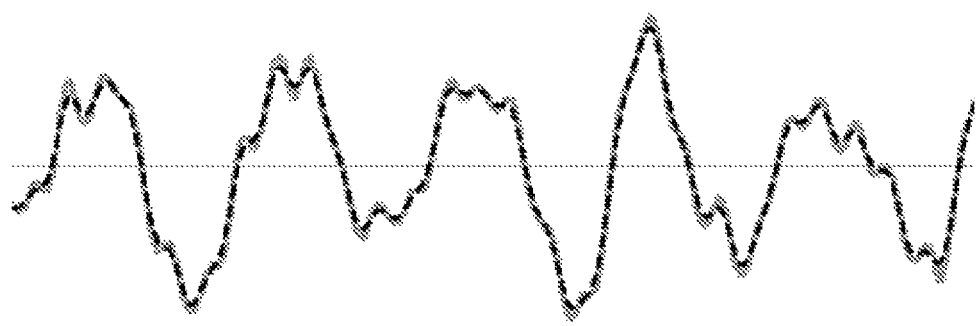
FIG. 6B   segmentation guide function g1
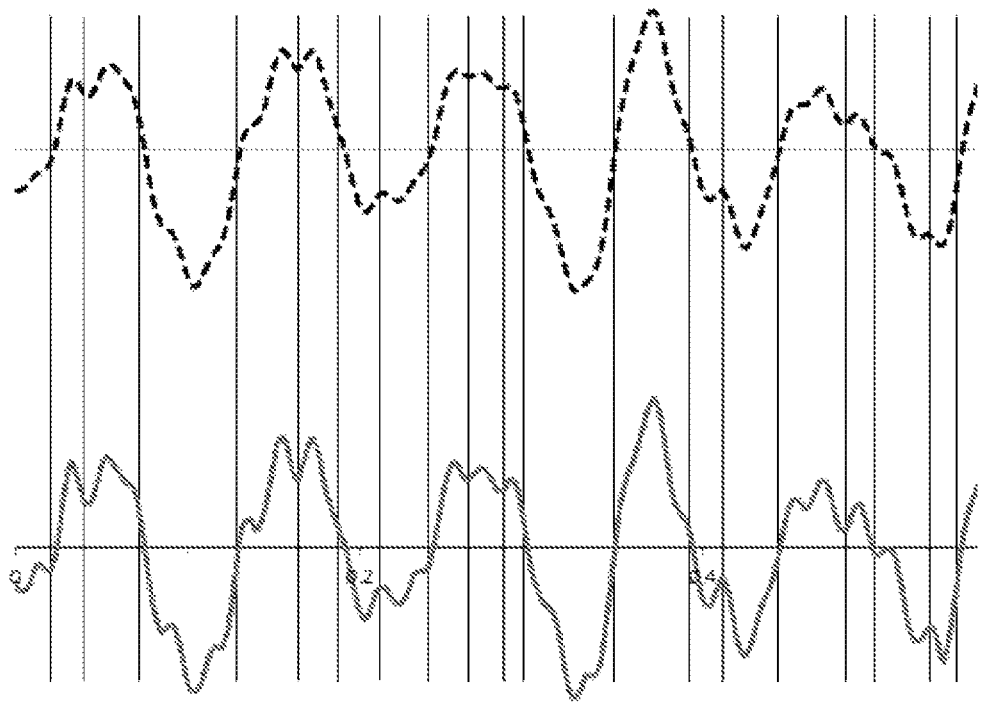
FIG. 6C

Low resolution segmentation
FIG. 7A
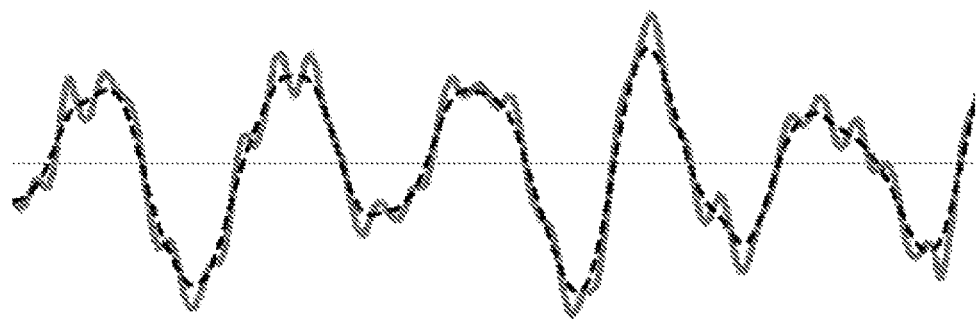
FIG. 7B  segmentation guide function g2
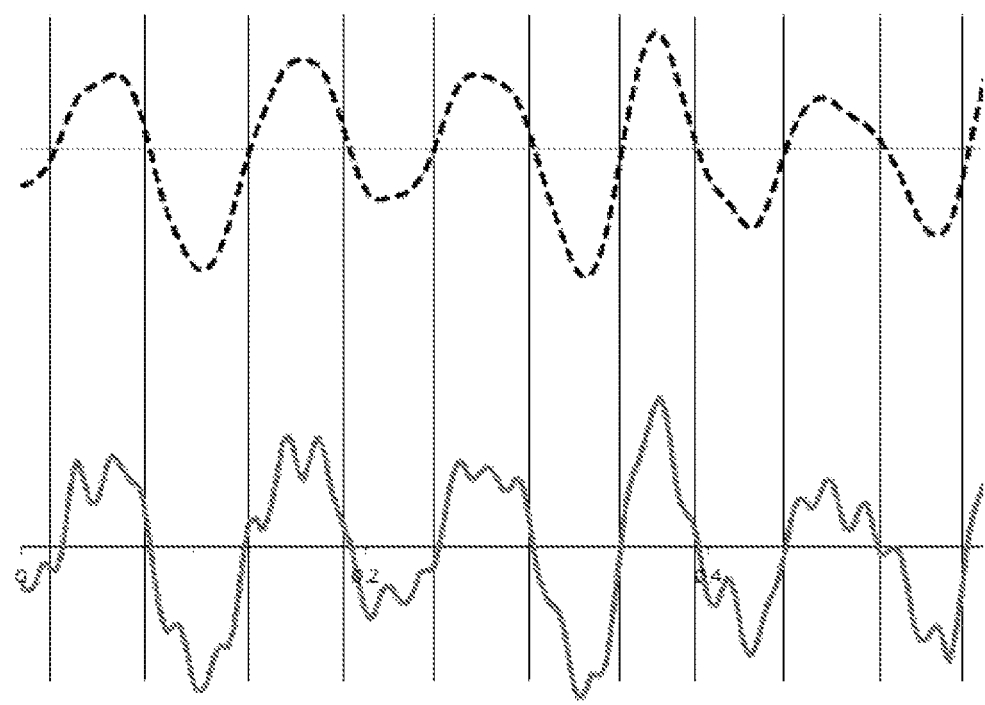
FIG. 7C

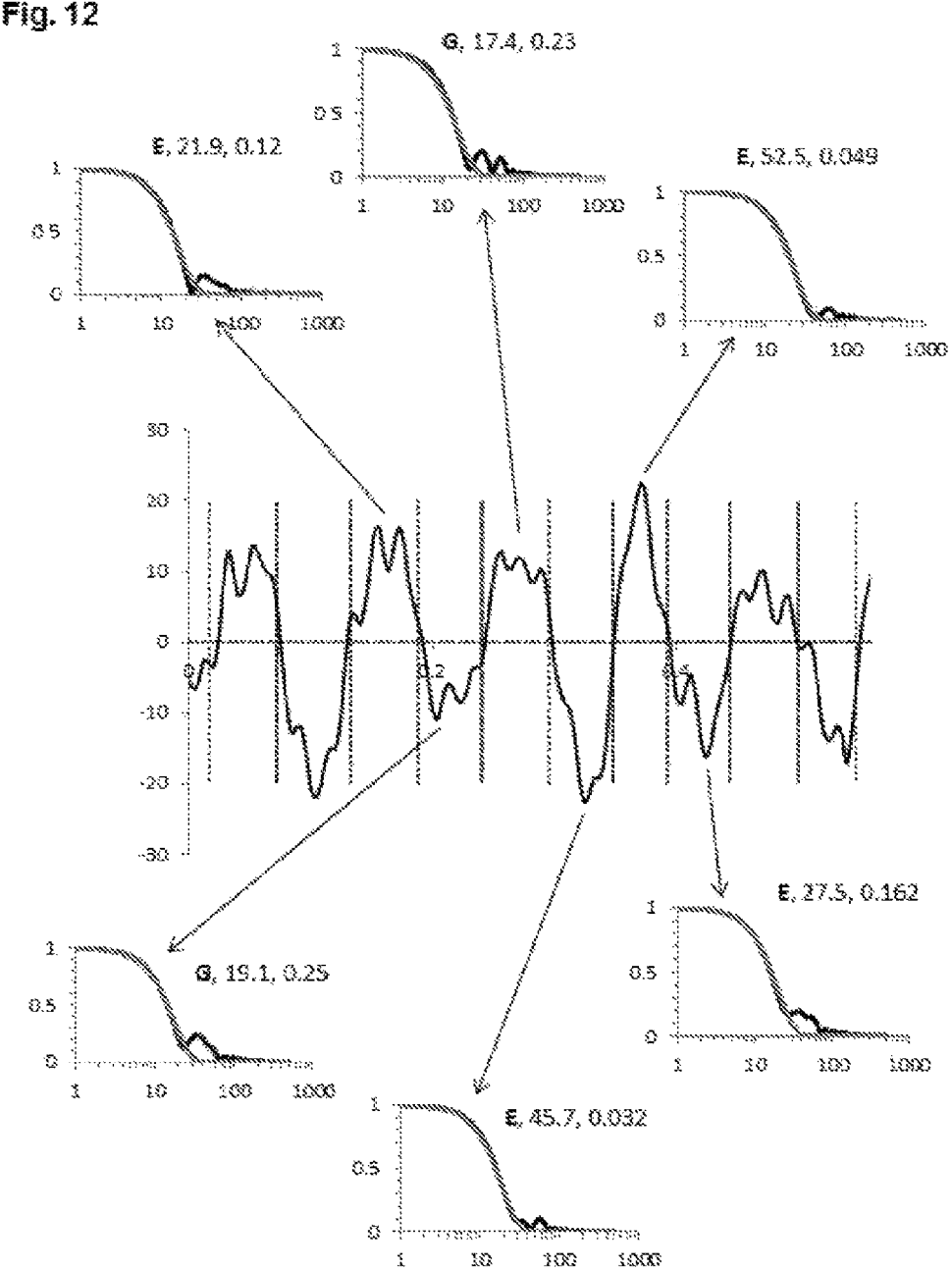

DECOMPOSITION OF NON-STATIONARY SIGNALS INTO FUNCTIONAL COMPONENTS

CROSS-REFERENCE TO RELATED APPLICATIONS

This application is a national stage (under 35 U.S.C. 371) of International Patent Application No. PCT/AU2014/050283, filed Oct. 13, 2014, which claims priority to Australian Patent Application No. 2013903948, filed Oct. 14, 2013, both of which are herein incorporated by reference in their entirety.

FIELD OF THE INVENTION

The present invention relates generally to signal processing and, in particular, to decomposing non-stationary biomedical signals into functional components, and to estimate parameters characterizing each of those functional components.

BACKGROUND

Non-stationary signals are produced by systems with attributes that vary with time. The necessity to understand and analyze such non-stationary signals from theoretical, research and diagnostic standpoints emerges in almost every field of biomedical research. However, non-stationary signals are not supported by general signal theory, and suitable mathematical methods to deal with non-stationary signals are quite limited.

Current signal processing methods are generally routed in the theory of linear stationary systems. Accordingly, the non-stationary character of real data is often ignored or the effects presumed to be negligible. Although the corresponding assumptions of the time invariance and linearity provide acceptable results for some applications, many physiological phenomena are highly variable and nonlinear, and therefore do not admit a reasonably accurate linear approximation. Meanwhile, a large body of scientific and clinical evidence indicates that a more comprehensive analysis of major non-stationary physiological signals, such as electrocardiogram (ECG) and electroencephalogram (EEG), is expected to lead to a deeper understanding of the mechanisms and states of various physiological systems under different normal and pathological conditions. In this context, developments of advanced algorithms of non-stationary signal processing emerge as capable approaches to a number of increasingly challenging applications, such as human brain and body imaging, computer implemented health monitoring and EEG based brain-computer interfaces. At the same time, the ongoing advances of computerized biomedical systems, in terms of speed, size, and cost, made the development of sophisticated algorithms practical and cost effective.

Non-stationary signal analysis is not supported by adequate theoretical and computational frameworks, such as in the case of linear stationary systems theory. A heuristic, rather than a mathematically rigorous approach, is generally accepted in the analysis of particular types of physiological signals. For example, when analyzing EEG signals, such signals may be analyzed using the notion of local stationarity (see Barlow, J. S. "Methods of analysis of non-stationary EEGs, with emphasis on segmentation techniques: a comparative review". J. Clin. Neurophysiol. 1985, vol. 2, pp. 267-304). This notion presumes that, although the signal is inherently non-stationary, within small intervals of time the signal pattern departs only slightly from stationarity (see Priestley, M. B.: "Non-Linear and Non-Stationary Time Series Analysis", Academic Press, London, 1988). Such quasi-stationary elements are associated with different components of the signal that may be produced by distinct non-linear systems.

So far, the problem of detecting components of non-stationary signals has been approached using data driven and model driven signal processing methodologies.

The advantage of data-driven signal processing methods is their ability to describe dynamics of complex empirical waveforms in detail. One such data-driven method, the empirical mode decomposition (EMD), has been developed by Huang et al. (Huang et al.: "The empirical mode decomposition and the Hilbert spectrum for nonlinear and non-stationary time series analysis". Proc. R. Soc. London, Ser. A, 1998, vol. 454, pp. 903-995) to decompose on an adaptive basis a non-stationary signal into the sum of "well-behaved" oscillatory functions, termed intrinsic mode functions. In the following developments the EMD has been supported by the Hilbert transform which provided instantaneous frequencies for each intrinsic mode function. Using these measures, the technique describes the system in terms of the instantaneous frequency changes. Yet, the solution is not uniquely defined because it depends on a number of empirical parameters, the choice of which is not supported by strict criteria. Without a firm mathematical foundation of the EMD, this purely empirical and intuitive approach creates a number of difficult methodological problems. For example, the intrinsic mode function is defined only numerically as the output of an iterative algorithm, with no analytical definition. Under these circumstances, the judgments about different aspects of methodology have come from case-by-case comparisons conducted empirically.

The model-driven approach to bio-medical signal processing requires accurate models of the systems involved. A specific aspect of the problem is that physiological signals are the global scale variables produced by multiple microscopic scale sources. Creation of a physical model necessitates a strict identification of relevant microscopic scale elements and the synthesis, on these grounds, the global model. However, the transition from the global to the microscopic scale using these strictly deterministic notions has no unique solution because it is impossible to exactly delineate a distinctive pattern of the cellular and molecular phenomena involved. In the face of such uncertainty, numerous efforts to create models of the cellular machinery that gives rise to the global scale signals are supported by a remarkable variety of heuristic approaches that differ widely not only in physiological and anatomical details of the models, but also in the basic mathematical tools. The extent to which the models are in contradiction is unknown.

Accordingly, there still exists a need, unfulfilled by current methodologies, to effectively identify components of a non-stationary time series signal, so that the corresponding models can be efficaciously utilized for classifying the attributes of the signal.

SUMMARY

It is an object of the present invention to substantially overcome, or at least ameliorate, one or more disadvantages of existing arrangements.

According to a first aspect of the present invention, there is provided a method of decomposing a non-stationary signal into the set of self-similar functional components with the quasi-Gaussian kernel (QGK) as a basis element, and for estimating parameters characterizing respective functional components, the method comprising the steps of:

estimating dynamic and baseline trends in the time course of the non-stationary signal, extracting the guide function and its adaptive segmentation;

dividing the non-stationary signal into the regions of component development;

recursively compensating for overlap from QGKs matched to preceding functional components to form an empirical component kernel (ECK) at each cycle of recursion, the sub-steps of:

transforming the ECK to a frequency domain;

estimating the parameters of QGK and their validation; and creation of global and partial models of the non-stationary signal.

According to another aspect of the present invention, there is provided an apparatus for implementing the aforementioned method.

Other aspects of the invention are also disclosed.

BRIEF DESCRIPTION OF THE DRAWINGS

One or more embodiments of the present invention will now be described with reference to the drawings, in which:

FIG. 2A illustrates a typical ERP signal elicited in an auditory oddball paradigm;

FIG. 2B illustrates typical results of substituting each segment shown in FIG. 2A with a quasi-Gaussian kernel having parameters that matches that segment;

FIG. 2C illustrates the model obtained as the sum of component quasi-Gaussian kernels, as well as the original ERP signal shown in FIG. 2A for comparison;

FIGS. 5A and 5B illustrate segmentation points resulting from zero-crossings and points of global and local minimums respectively;

FIG. 5C shows an example of EEG signal segmentation with zero-crossings and minimums illustrated by solid and dotted vertical lines respectively;

FIG. 6A shows an initial signal and a guide function that provide segmentation points with high temporal resolution;

FIGS. 6B and 6C replicate the guide function and initial signal from FIG. 6A with segmentation points indicated by vertical lines;

FIG. 7A shows the initial signal from FIG. 6A and the guide function that provides signal segmentation with low temporal resolution;

FIGS. 7B and 7C replicate the guide function and initial function from FIG. 7A with segmentation points indicated by vertical lines;

FIG. 12 exemplifies several results of the amplitude template matched to the normalized amplitude spectra of different segments of the EEG signal shown in the middle panel of the figure;

DETAILED DESCRIPTION

Figure 1A:
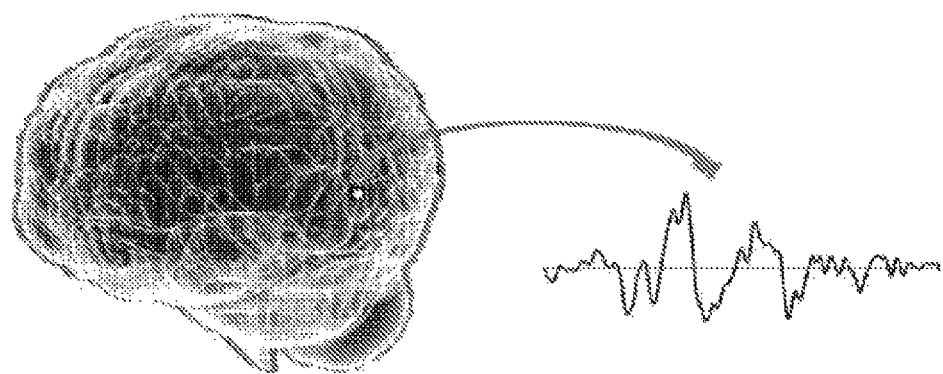
FIG. 1A illustrates a typical form of an electrical potential measured between two sensors placed on the surface of a scalp.

Where reference is made in any one or more of the accompanying drawings to steps and/or features, which have the same reference numerals, those steps and/or features have for the purposes of this description the same function(s) or operation(s), unless the contrary intention appears.

To describe a non-stationary signal, a crucial step is to create a model. Conventional approaches to this problem are supported by "physics-based" models: the aim being to describe the signal in terms of an explicit physical model of its sources (see Candy J. V. "Model-based signal processing". John Wiley & Sons, New Jersey, 2006). However, non-stationary signals are usually produced by multiple non-linear sources, the functionality of which remains unclear.

In contrast to these physics-based approaches, the method disclosed herein is supported by a chaos-based modeling (CBM) approach. Such take combined account of both deterministic and probabilistic factors that define the source behaviour. The general framework of this approach is introduced by reference to the general mechanisms underlying the genesis of biomedical signals.

A general aspect of biomedical signal analysis is that physiological process is a global scale variable produced by multiple elementary sources acting on the macroscopic scale. In this context, physiological processes reflect the external performance of monumentally complex systems of molecular and cellular elements, the performance of which is governed by both deterministic and stochastic factors. A major difficulty lies in the fact that models of relevant cellular ensembles are not feasible, as the number of functional elements required is too high and the details of the cellular machinery are too intricate. However, numerous theoretical and computational studies of the mass effect produced by multiple microscopic scale variables shed some light on those general aspects of the cellular machinery that are significant on the global scale from those that are not. Thus, a general physical concept is that a synchronous activation of a large number of elementary sources in a local microscopic scale volume is a necessary condition to produce a detectable change in the signal measured at the global scale. Major aspects of these processes have been broadly studied for such clinically important biomedical signals as the electroencephalogram (EEG), electrocardiogram (ECG) and electromyogram (EMG). The general framework that suggests a peaking global scale waveform as a marker of a distinct physiological component may be illustrated by reference to the mechanisms underlying the EEG genesis.

As illustrated in FIG. 1A, the EEG may be measured using sensors placed on the surface of a scalp. The electrical potential is caused by activity of neurons in the cortical areas of the brain below the scalp. The activity of a single neuron is not high enough to produce a measurable potential between the sensors placed on the surface of the scalp. Rather, when large ensembles of closely located cortical neurons work in synchrony, their summed activity produces extracellular dipoles from which the measured electrical potential results.

Figure 1B:
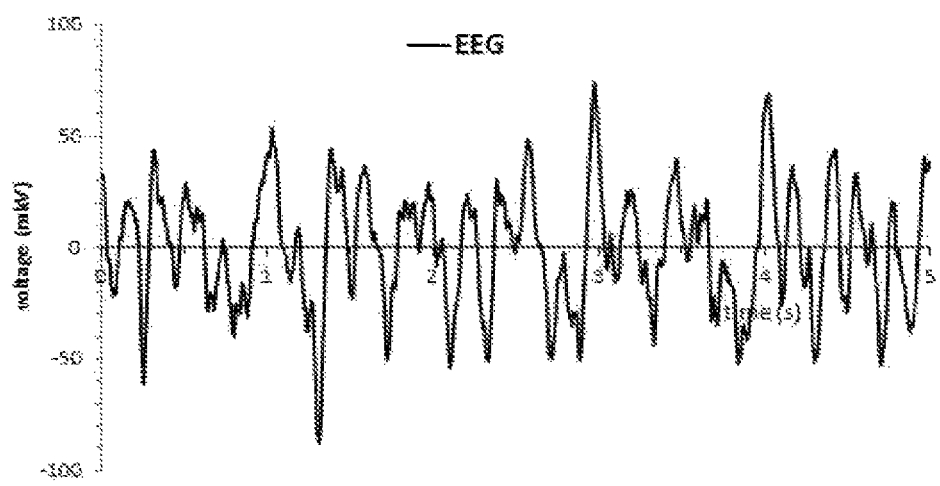
FIG. 1B exemplifies the highly non-stationary character of an EEG signal.

The fluctuations and dynamics of these mass potentials registered at the surface of the scalp follow the activity of cortical neural processors without time lags. In this context the EEG signals serve as one of the most important objective markers for real time studying the basic mechanisms of information processing in the human brain. An example of an EEG signal shown in FIG. 1B illustrates that electrical activity of the brain is typically both highly irregular and non-stationary, and produces a variety of activity patterns.

A key to the understanding of the information processing context of EEG signals is provided by detection of changes in the EEG signals, and their relationship in time with particular stimuli during a cognitive task. Such specific fragments of EEG signals are termed event related potentials (ERPs). FIG. 2A illustrates a typical ERP elicited in an auditory oddball paradigm. The oddball paradigm is a test during which the character of the EEG signal is affected by the application of two types of auditory tones, namely background and target stimuli. In the EEG signal illustrated in FIG. 2A, the target stimulus is applied at t=0. This event is followed by a succession of positive and negative waveform deflections. On the grounds of significant experimental and clinical evidence, the waveform peaks that appear at specific time intervals after application of the stimulus are regarded as functional entities associated with various cortical neuronal networks. In the auditory oddball paradigm, such peak potentials are known as the late latency ERPs denoted as N100, P200, N200 and P300 respectively. The number is representative of an approximate time (in milliseconds) of a negative (N) or positive (P) peak appearance after the stimulus application. A specific aspect of P300 is that when examining averages of repeated ERPs, this late latency component appears as a monolithic peak. However, when examining a single ERP waveform, i.e. the original EEG signal, the late latency ERP P300 usually appears as a complex potential that consists of two sub-components denoted P3a and P3b.

Distinct positive-negative fluctuations labelled in such a manner appear as objective markers of serially activated processes that are intimately related to important physiological systems. The concept of a peaking waveform as a marker of a component produced by a functional system with specific structure-function organization is conventionally applied to almost all physiological processes of significant scientific and clinical importance. Given this widely accepted approach, the variety of different manual or computer implemented measurement techniques (peak picking procedures) reduce the physiological signal to the peak amplitudes and peak latencies. A critical limitation of these largely empirical techniques is that reduction of a signal to peak amplitudes and latencies at isolated time points is unable to characterize the dynamics of biological waveforms that contain important functional and clinical information. In a computational context, the drawback of all these techniques is their inability to resolve component temporal overlap. Without overlap corrections, the measurements of amplitude and latency parameters may be affected by significant uncontrolled errors.

Figure 3:
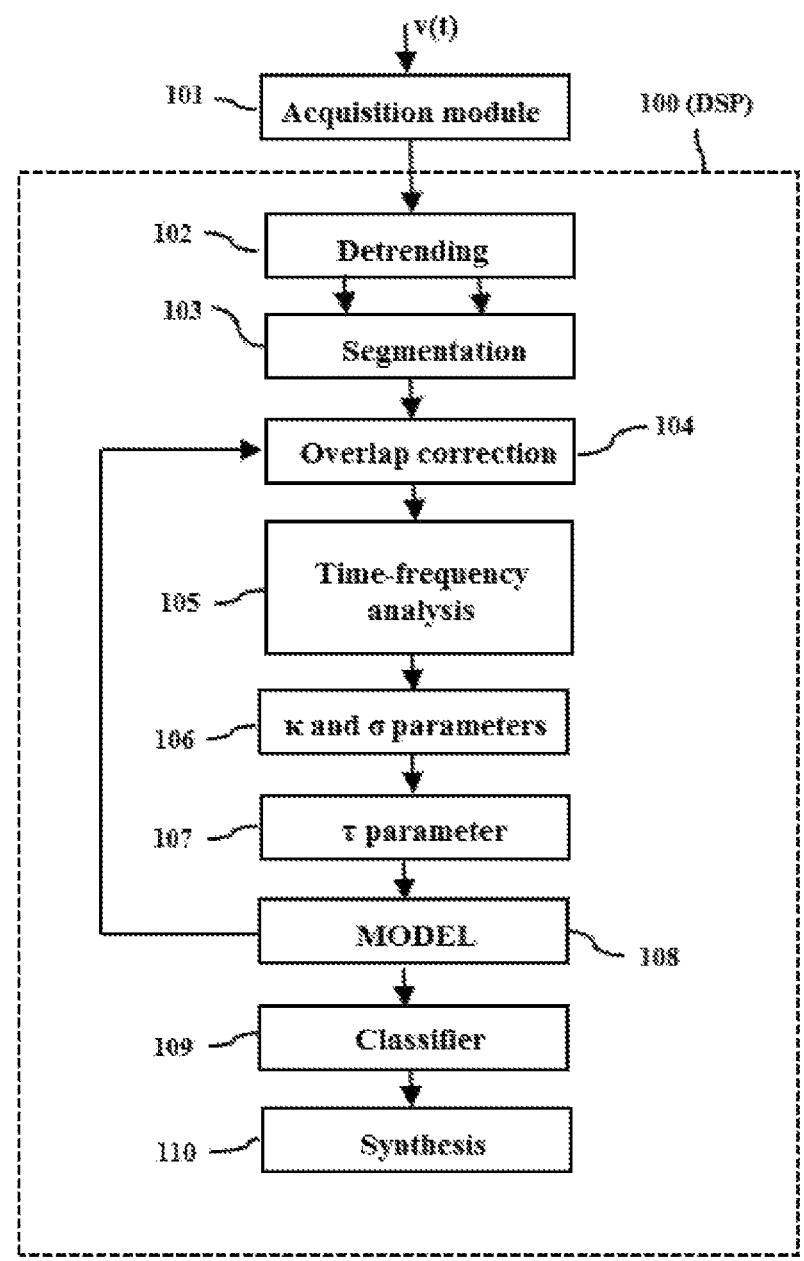
FIG. 3 shows a schematic flow diagram of a method of waveform analysis which adaptively decomposes a physiological signal into functional components, and then determines parameters characterizing each functional component.

FIG. 3 shows a schematic flow diagram of a method 100 of waveform analysis which regards a component as not just being a peak in the waveform, but a deflection (positive or negative) with a specific shape. More particularly, method 100 adaptively decomposes a non-stationary signal v(t) into functional components, and then applies time-frequency analysis and parameter estimation procedures to identify each functional component in terms of dynamic model and relevant parameters. The non-stationary signal v(t) may be an EEG signal, an electrocardiogram (ECG) signal, an electromyogram (EMG) signal, a signal derived from breathing, etc.

The method 100 may be implemented using software, such as one or more application programs, executed within a computer system. The method 100 may alternatively be implemented in dedicated hardware, such as one or more integrated circuits, performing the functions or sub functions of the method 100. Such dedicated hardware may include digital signal processors, or one or more microprocessors and associated memories.

The method 100 starts in step 101 where the non-stationary signal v(t), which is an analogue signal, is conditioned to form a discrete input sequence consisted of sampled values $v_m = v(t_m)$. More particularly, the non-stationary signal v(t) is amplified within a range of standard voltages, and sampled at regular sampling intervals $t_m = m\Delta$, where m is an integer and $\Delta$ is the sampling interval. This produces a set of samples $v = \{v_0, \ldots, v_m, \ldots, v_M\}$. The non-stationary signal v(t) may be regarded as a band-limited signal, and the sampling interval $\Delta$ is chosen to exceed the Nyquist rate, being the lowest sampling rate that is necessary for accurate restoration of the sampled non-stationary signal v(t).

As is described in detail below, the method 100 then operates on the discrete input sequence $v = \{v_0, \ldots, v_m, \ldots, v_M\}$, being the discrete representation of the non-stationary signal v(t), to divide the input sequence $v = \{v_0, \ldots, v_m, \ldots, v_M\}$ into segments, to apply time-frequency analysis to each segment and to identify for each segment the dynamic model with parameters matched to the segment. A sequence of parameters is so formed, and that sequence of parameters is used to classify each segment according to user defined criteria and also synthesis the non-stationary signal v(t) or its defined segments.

The non-stationary signal v(t), and thus also its discrete counterpart $v=\{v_0, \ldots, v_m, \ldots, v_M\}$, typically contains high frequency noise and low frequency background activity. These irrelevant activities are usually removed from further analysis using low-pass and high-pass filters. However, due to the highly irregular and non-stationary nature of both meaningful functional components and irrelevant activities, the application of filters with time invariant frequency characteristics may significantly and unpredictably distort the dynamics of functional components, with the loss of functionally important information.

A general solution to this problem is to use an adaptive filter. Such an adaptive filter must adapt its performance to changing trends in signal dynamics. The digital filler most commonly used for trend estimation, the moving average or boxcar filter, is a digital filter with finite impulse response which replaces each sample with the average of the sample in question and a given number of consecutive previous and subsequent points. However, the frequency response of the boxcar filter is far from optimal and simple moving averaging may cause substantial distortions in the trend trajectories. To avoid such distortions, step 102 uses a multiple-pass moving average (MPMA) filter for removing the high frequency noise and low frequency background activity from the input sequence v. More particularly, two MPMA filters are applied to the input sequence v for estimation of dynamic and baseline trends in the input sequence v.

The MPMA is an iterative process, each iteration of which applies moving window averaging to an input sequence, with the input sequence of the first iteration being the input sequence v, and the input sequence of subsequent iterations being the result of the preceding iteration. Accordingly, in the k-th iteration, the input and output sequences are $v^{k-1}=\{v_0^{k-1}, \ldots, v_m^{k-1}, \ldots, v_M^{k-1}\}$ and $v^k=\{v_0^k, \ldots, v_m^k, \ldots, v_M^k\}$ respectively, where the number of samples is M+1, k from 1 to K is the number of the iteration, and $v^0=v$.

The output sequence $v^{k+1}$ for the mth sample is given by the following:

$$v_m^{k+1} = \frac{1}{2P+1} \sum_{j=-P}^{P} v_{m+j}^k, \quad (1)$$

where P defines the width of the window, the width of the window being $N_w=2P+1$.

It is clear from Equation (1) that $v_m^{k+1}$ is defined by P consecutive previous points and P consecutive subsequent points. However, according to the definition of sequence v, the first sample of the processes in question is $v_0^{k+1}$. Consequently, the values $v_{m+j}^k$ with m+j<0 are excluded from calculations. This may be regarded as zero padding that consists of extending sequence v with zero values $v_n=0$ for n from −1 to −P.

Whereas conventional moving window averaging produces high-frequency distortions in a spectrum of the resulting sequence, the MPMA applied in step 102 gradually removes such distortions from the spectrum. Residuals Δ $v_m^{k+1}=|v_m^{k+1}-v_m^k|$ with m from P to M−P decrease following each iteration. An improvement in the trend estimation after the k-th iteration is evaluated by measuring the change of sampled values between iterations. The accuracy is expressed in terms of the following mean square error:

$$\delta_S = \frac{1}{M-2P+1} \sum_{m=P}^{M-P} (v_m^{k+1}-v_m^k)^2. \quad (2)$$

The iterations are terminated when a desired improvement is achieved. When applied to typical electrophysiological signals, such as EEG, ERPs EMGs and ECGs, the iterations are terminated after the k-th iteration if:

$$\frac{\sqrt{\delta_S}}{M_v} < Tr, \quad (3)$$

where $M_v$ is the mean value of the output signal $v^k$, and Tr is the dimensionless threshold. Given 0.05 as a reasonable threshold Tr in these applications, the iterations are typically terminated after 5 iterations.

Figure 4A:
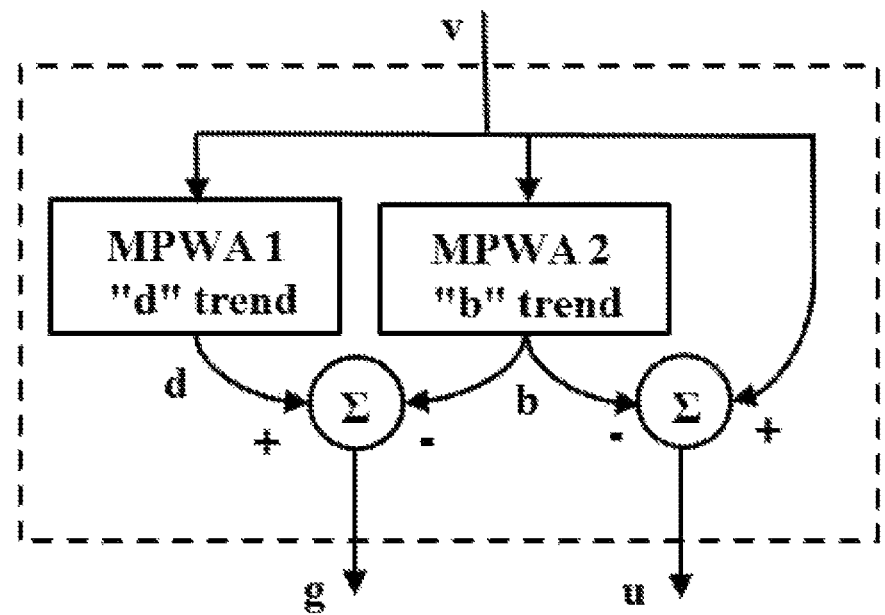
FIG. 4A shows a schematic flow diagram of dynamic and baseline trend estimation applied in the method shown in FIG. 3.

FIG. 4A shows a schematic flow diagram of the dynamic and baseline trend estimation applied in step 102. Two separate MPMAs are applied on the input sequence v in units MPMA 1 and MPMA 2 to form filtered sequences: dynamic trend $d=\{d_0, \ldots, d_m, \ldots, d_M\}$ and baseline trend $b=\{b_0, \ldots, b_m, \ldots, b_M\}$. MPMA 1 and MPMA 2 have different window parameters. $N_{W1}$ and $N_{W2}$, that must satisfy the condition $N_{W2} \geq N_{W1}+2$. The input sequence v and filtered sequences d and b are then combined to produce two output sequences g and u.

The sequence $u=\{u_0, \ldots, u_m, \ldots, u_M\}$, with $u_m=v_m-b_m$, represents a baseline re-trended signal, i.e. the primary sequence v after subtraction of the baseline trend b.

Figure 4B:
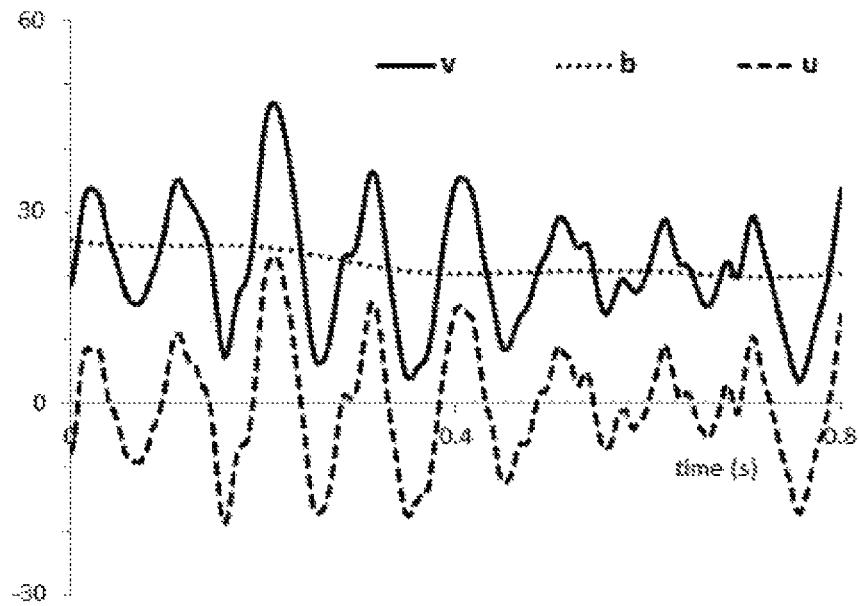
FIG. 4B shows a typical physiological signal, a baseline trend resulting from applying multiple-pass moving window averaging to the discrete physiological signal, and a baseline de-trended signal.

FIG. 4B exemplifies the calculation of the baseline de-trended physiological signal u. The solid line is a 201 point portion of a typical EEG signal v sampled at Δ=0.004 s. The dotted line is the baseline b resulting from applying the MPMA 2 with a 31 point window and using 5 iterations. After removal of the baseline b from the EEG signal v, the de-trended sequence u is shown by the dashed line.

The sequence $g=\{g_0, \ldots, g_m, \ldots, g_M\}$, with $g_m=d_m-b_m$, is termed a guide function. The guide function is obtained using the removal of irrelevant high- and low-frequency components from the time course of the signal. These purifying operations support the role of sequence g as a guide for the search of meaningful functional components.

Referring again to FIG. 3, following the de-trending in step 102 the method continues to step 103 where segmentation is performed on the guide function g. The objective of the segmentation performed in step 103 is to estimate segmentation points which define the signal segments associated with functional components. The segmentation points are defined as zero-crossings (ZC) illustrated in FIG. 5A and points of global and local minimums of the modulus of the guide function illustrated in FIG. 5B. FIG. 5C shows an example of the guide function g with zero-crossings illustrated in vertical solid lines and minimums illustrated in vertical dashed lines.

More particularly, point $t_m$ is qualified as a zero-crossing if:

$$(g_{m-1} \leq 0 \text{ AND } g_{m+1} > 0) \text{ OR } (g_{m-1} \geq 0 \text{ AND } g_{m+1} < 0) \quad (4)$$

The point $t_m$ specifies a global or local minimum of $|g|=\{|g_0|, \ldots, |g_m|, \ldots, |g_M|\}$ if:

$$|g_{m-1}| \geq |g_m| \leq |g_{m+1}|. \quad (5)$$

A sequence of segmentation points $\{\chi_0, \ldots, \chi_i, \ldots, \chi_N\}$ is so formed, with the lengths $\lambda_1, \ldots, \lambda_i, \ldots, \lambda_N$ of the segments defined by the segmentation points $\{\chi_0, \ldots, \chi_i, \ldots \chi_N\}$ being:

$$\lambda_i = \chi_i - \chi_{i-1} (i=1, \ldots, N) \quad (6)$$

Generally, the guide function g may be regarded as an approximant to the de-trended signal u. The accuracy of approximation is modifiable using different parameters of the MPMA 1. Accordingly, the temporal resolution of the segmentation procedure is governed by an appropriate choice of the parameters of the MPMA 1.

FIGS. 6A and 7A illustrate two guide functions (dash lines) calculated for one and the same de-trended EEG signal u (grey lines) using different parameters for MPMA 1. More particularly, the guide functions g1 and g2, separately shown in FIG. 6B and FIG. 7B, have been calculated using 3 and 7 point windows, respectively. Both cases have been calculated using 2 iterations. The results displayed in FIG. 6A indicate a minor discrepancy between the de-trended sequence u and guide function g1. Thus the guide function g1 reproduces the de-trended signal in detail, and consequently may be regarded as a practically precise reproduction of the de-trended sequence u. The segmentation points indicated by vertical lines include 11 zero-crossing and 8 minimums.

By contrast, the results displayed in FIG. 7A, and also comparison of FIG. 6B with FIG. 7B, shows that the same MPMA procedure with a larger window removes minimums from the segmentation points and as a result replaces complex peaking waveforms by monolithic waveforms. In some cases the significance of the process is that it removes functionally irrelevant activities, and emphasises dominant dynamic trends in the time domain of a global scale physiological signal such as EEG, EMG, ECG, etc. However, irregular high frequency signal fluctuations may be produced by physically significant sources. For example, in the case of EEG activities with frequencies higher than 30 Hz are known as gamma rhythms. Therefore, depending on the character of application, both the high resolution segmentation and low resolution segmentation, as well as their different combinations provide powerful computational tools for the investigation of the component composition of complex non-stationary signals.

Although the signal transformations applied in step 103 are performed in the time domain, they may also be associated with frequency domain notions. As is clear from FIGS. 6A and 7A, the narrow window used in MPMA 1 performs low-pass filtering with a higher frequency bandwidth, whereas the wide window used in MPMA 2 perform low-pass filtering with a relatively low frequency bandwidth. However, since the original signal is a non-stationary process, the employment of conventional frequency bands with fixed "cutoff" frequencies is ambiguous.

Referring again to FIG. 3, following the segmentation in step 103 the method 100 performs steps 104 to 108 as a recursion, consecutive cycles of which deal with the succession of defined signal segments. For each segment a component model is identified, the parameters of which are matched to the corresponding signal fragment. Since the respective component model matched to the signal in that segment extends into following segments, the aim of recursion steps from 104 to 108 is also to resolve temporal component overlap. Resolution of the component temporal overlap is a pressing problem in many fields of signal processing that is not supported by common methods. A major difficulty is that any approach to this problem must involve creation of the component model in order to describe predictable structures and expected patterns in the component development, and to forecast the future values of the component from its past trajectory.

The drawback of a "physics-based" approach (see Candy J. V. "Model-based signal processing". John Wiley & Sons, New Jersey, 2006) lies in the fact that usually not enough information is available regarding the signal in terms of explicit physical models of its sources. By contrast to the physics-based approaches, the method disclosed herein introduces a unique methodology of chaos-based modeling (CBM) which defines major components of a non-stationary signal in terms of deterministic chaos. This chaos based modelling approach has been encouraged by the empirical finding of the normalization effect (see Melkonian D. Blumenthal T, Gordon E. "Numerical Fourier transform spectroscopy of EMG half-waves: fragmentary-decomposition-based approach to nonstationary signal analysis". Biol Cybem., 1999, vol. 81, pp. 457-467). The finding indicates that due to an interference of deterministic and random factors the source activity from the microscopic scale is converted at the global scale to statistical measures which reflect probabilistic regularities rather than a physical nature of the elementary sources. Thus, a global scale physiological component develops as a cumulative statistical aggregate of multiple elementary sources.

To formulate a universal global scale component model on this heuristic basis, the method refers to the central limit theorem as a tool that defines the limiting behavior of ensembles of random variables (see Gnedenko B, Kolmogorov A. "Limit distributions for sums of independent random variables". Addison-Wesley Publishing Company, Reading, Mass., 1954). Given the sum of a certain number of random variables $f_1, f_2, \ldots, f_n$ with means $\eta_1, \eta_2, \ldots, \eta_n$ and variances $\sigma_1^2, \sigma_2^2, \ldots, \sigma_n^2$, the limiting behavior of their exponential Fourier transforms $F_1(i\omega)$, $F_2(i\omega), \ldots, F_n(i\omega)$ converge under quite general conditions to a Gaussian function as n→∞ (see Papoulis A. "The Fourier integral and its applications". McGraw-Hill Book Co, NewYork, 1962)

$$F(i\omega) \Rightarrow e^{-\frac{\sigma^2\omega^2}{2} - i\eta\omega} \quad (7)$$

where $F(i\omega)$ is an exponential Fourier transform (function of complex variable $i\omega$, $i=\sqrt{-1}$), $\eta=\eta_1+\eta_2+ \ldots +\eta_n$ and $\sigma^2=\sigma_1^2+\sigma_2^2+ \ldots +\sigma_n^2$.

Thus, the effects of single sources are transformed into the summary parameters σ and η that have meaning as global scale variables.

In physical terms, $$F(\omega) = |F(i\omega)| = e^{-\frac{\sigma^2\omega^2}{2}} \quad (8)$$

may be regarded as the amplitude spectrum of a global scale temporal process produced by the multiplicity of microscopic scale sources.

Empirical support of this theoretical prediction has been provided by the study of auditory event related potentials (see Melkonian D, Gordon E, Rennie C, Bahramali H. Dynamic spectral analysis of event-related potentials. Electroencephalography and Clinical Neurophysiology, 1998, vol. 108, pp. 251-259). Dynamic spectral analysis revealed that a Gaussian function provides a universal description of the profiles of the amplitude spectra of the main late latency components of the auditory event related potentials.

The time domain counterpart of the frequency domain complex spectrum of Equation (7) is defined in relevant literature on an infinite time scale interval. Similarly to Equation (8), the time domain solution tends also to a Gaussian function of the following form:

$$f(t) \Rightarrow \frac{1}{\sigma\sqrt{2\pi}} e^{-\frac{(t-\eta)^2}{2\sigma^2}}. \qquad (9)$$

In contrast, the signal processing routines of the disclosed method deal with causal time functions that may be regarded as transients in physically realizable systems.

To relocate the time domain analysis from an infinite to semi-infinite time scale the disclosed method introduces a causal function w(t) which is defined at t≥0 as the sum of two Gaussian functions $$w(t) = [g_A(t) - g_B(t)] \cdot U(t) = g(t) \cdot U(t) \qquad (10)$$
where
$$g_A(t) = \frac{1}{\sigma\sqrt{2\pi}} \left[ \exp\left( -\frac{(t-\varepsilon\sigma)^2}{2\sigma^2} \right) \right] \qquad (11)$$

$$g_B(t) = \frac{1}{\sigma\sqrt{2\pi}} \left[ \exp\left( -\frac{(t+\varepsilon\sigma)^2}{2\sigma^2} \right) \right] \qquad (12)$$

$$U(t) = \begin{cases} 1 & \text{if } t \geq 0 \\ 0 & \text{otherwise} \end{cases} \qquad (13)$$

in which U(t) is a unit step function, and e is a dimensionless constant.

Comparing Equation (7) with Equations (11) and (12) shows that parameter η (mean) from Equation (7) is expressed in Equations (11) and (12) as the fraction of the parameter σ (dispersion) using the constant ε. The value of constant ε depends on the type of a non-stationary signal. Thus, the analysis and computer simulations of human and animal EEGs using the disclosed method suggest ε=2 as a universal constant for these applications. This estimate is regarded as default value of constant ε.

Figure 8A:
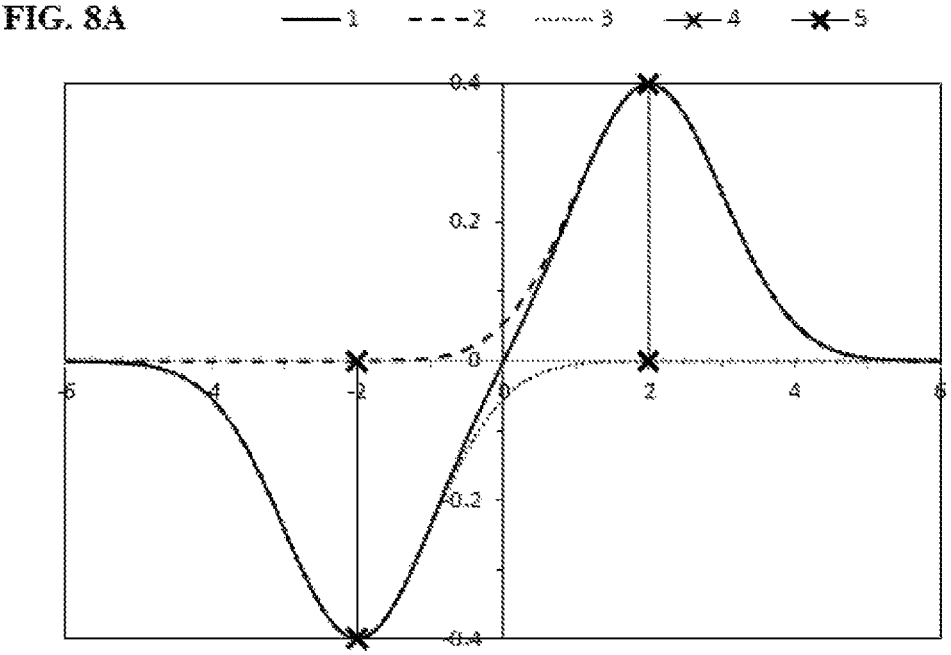
FIG. 8A illustrates Gaussian components used for composition of a quasi-Gaussian kernel.

Functions $g_A(t)$ and $-g_B(t)$ with the parameter σ=1 and constant ε=2 are shown in FIG. 8A by the dash and dotted lines, respectively. The extremes of these functions are at t=εσ and t=−εσ.

Shown by the solid line in FIG. 8A, function g(t) is an odd function of infinite extent. The Fourier transform of the function g(t) is:

$$G(i\omega) = \int_{-\infty}^{\infty} g(t)e^{-i\omega t}dt = G_C(\omega) - iG_S(\omega) \qquad (14)$$
where $$G_C(\omega) = \int_{-\infty}^{\infty} g(t)\cos(\omega t)dt \qquad (15)$$

$$G_S(\omega) = \int_{-\infty}^{\infty} g(t)\sin(\omega t)dt. \qquad (16)$$

Since g(t) is an odd function, $G_C(\omega)=0$ and $$G_S(\omega) = 2\int_0^{\infty} g(t)\sin(\omega t)dt = 2\int_0^{\infty} w(t)\sin(\omega t)dt. \qquad (17)$$

The last trigonometric integral from Equation (17) is the Fourier sine transform of w(t) for which the denotation $$W_S(\omega) = \int_0^{\infty} w(t)\sin(\omega t)dt \qquad (18)$$

is used.

After replacement of w(t) by Equation (10), this integral is expressed analytically in the following form (see Erdelyi, A. (Ed). "Tables of integral transforms", Vol. 1. McGraw-Hill, New York, 1954, p. 78):

$$W_S(\omega) = e^{-\frac{(\sigma\omega)^2}{2}} \sin(\varepsilon\sigma\omega). \qquad (19)$$

This expression may be regarded as the imaginary part of the complex spectrum $$W(i\omega) = W(\omega)e^{-i\phi(\omega)} \qquad (20)$$
where $$W(\omega) = e^{-\frac{(\sigma\omega)^2}{2}} \qquad (21)$$

is the amplitude spectrum and $$\varphi(\omega)=\varepsilon\sigma\omega \qquad (22)$$

is the phase spectrum.

Figure 8B:
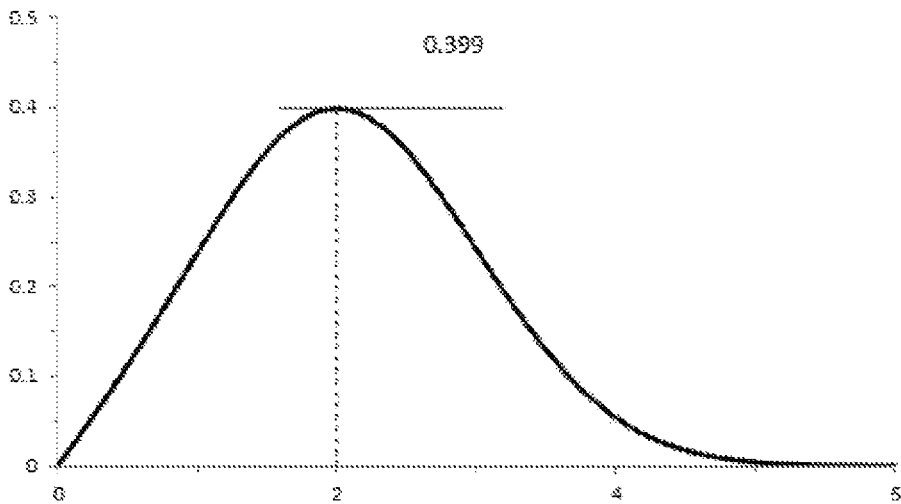
FIG. 8B illustrates an example quasi-Gaussian kernel.

Therefore, the duo of the frequency functions of Equations (21) and (22) may be regarded as the frequency domain counterparts that completely define the time domain signal of w(t) at t≥0. This function is shown in FIG. 8B. An approximate value at which w(t) reaches the maximum is t≈2. The value of the maximum w(2)≈0.399.

Physically, w(t) may be regarded as a transient process induced at t=0 by the activation of an ensemble of multiple microscopic scale sources. The behaviour of separate sources is governed by both probabilistic and deterministic factors and may be characterized as the deterministic chaos. A major characteristic feature of such form of behaviour is the non-linearity of the systems producing the deterministic chaos. In this context, the process described by Equation (11) may be regarded as an impulse response of a dynamic system governed by the following system of nonlinear differential equations:

$$\dot{g}_A(t) = -\frac{t-\varepsilon\sigma}{\sigma^2} g_A(t), \qquad (23)$$

$$\dot{g}_B(t) = -\frac{t+\varepsilon\sigma}{\sigma^2} g_B(t),$$

$$w(t) = g_A(t) - g_B(t),$$

where $\dot{g}_A(t)$ and $\dot{g}_B(t)$ denote the derivatives of $g_A(t)$ and $g_B(t)$.

The model of a composite non-stationary process is defined in the form:

$$v_N(t) = \sum_{i=1}^{N} \kappa_i w_i(t - \tau_i) = \sum_{i=1}^{N} \gamma_i(t), \qquad (24)$$

where $\kappa_i$ and $\tau_i$ are the free parameters termed the weight and onset time.

A component model termed a quasi-Gaussian kernel (QGK), is defined as:

$$\gamma_i(t) = \kappa_i w_i(t-\tau_i) \qquad (25)$$

which is characterised by a set of three parameters name $\langle \kappa_i, \sigma_i, \tau_i \rangle$.

In a general context, the stochasticity of $v_N(t)$ follows from the fact that parameters $\langle \kappa_i, \sigma_i, \tau_i \rangle$ are random variables. A specific aspect of the non-stationarity is that the structural composition of the system generating v(t) changes at the time instants $\tau_i$ when the new sources are connected to the underlying system. A crucial aspect of the deterministic chaos is exposed by the fact that though the Gaussian dependences of Equations (10)-(12) are deterministic processes, their temporal evolution develops as the limiting behaviour of the underlying elementary random events. Probabilistic aspects of relevant transformations at the microscopic scale have been formulated in terms of Markov processes, specifically non-homogenous birth and death processes (see Melkonian D, Blumenthal T. Dynamics of the eyeblink EMG at global and microscopic scales. The Open Cybernetics and Systemics Journal, 2013, vol. 7, pp. 11-22).

The method 100 performs steps 104 to 108 in order to identify parameters $\langle \kappa_i, \sigma_i, \tau_i \rangle$ of each QGK $\gamma_n(t)$ of Equation (24). The identification algorithm is organized as a recursion the guiding principle of which comes from the following relationship between the "n" and "n-1" terms of Equation (24):

$$v_n(t) = \sum_{i=1}^{n} \gamma_i(t) = v_{n-1}(t) + \gamma_n(t), \qquad (26)$$

Since function $v_n(t)$ is conceptually a model, this function $v_n(t)$ may be regarded as an approximant to the de-trended sequence u(t), i.e. $v_n(t) \cong u(t)$ at $t>0$. The contribution of the QGK $\gamma_n(t)$ to the approximant starts from the onset of $\gamma_n(t)$ at $t=\tau_n$. This means that $u(t) \cong v_{n-1}(t)$ for $0 \le t \le \tau_n$, $u(t) \cong v_{n-1}(t) + \gamma_n(t)$ for $0 \le t \le \tau_{n+1}$. $\qquad (27)$ Given $\tau_1 = 0$, $\gamma_1(t) \cong u(t)$ for $0 \le t \le \tau_2$. $\qquad (28)$ For $n>1$, $\gamma_n(t) \cong u(t) - v_{n-1}(t)$ for $\tau_n \le t \le \tau_{n+1}$ $\qquad (29)$ Equation (28) corresponds to the first cycle of recursion at which the impact of the previous terms is absent. Equation (29) corresponds to the nth cycle of recursion where the impact of the previous terms is accounted for by the function $v_{n-1}(t)$. This function is defined analytically by the major parameters $\langle \kappa_i, \sigma_i, \tau_i \rangle$ (i=1, ..., n-1) obtained at the previous cycles of recursion. The role of $v_{n-1}(t)$ is the correction of the temporal component overlap. In this context, the right hand part of the Equation (29) represents an overlap corrected semi-empirical counterpart of the analytical QGK $\gamma_n(t)$.

Parameters of QGK $\gamma_n(t)$ are interrelated in the time domain by complex non-linear relationships. The advantage of the frequency domain is that frequency domain relationships provide means to separate these relationships and to estimate the succession of $\kappa_n$, $\sigma_n$ and $\tau_n$ parameters by separate procedures performed in a consecutive order. An important aspect of the corresponding frequency domain manipulations is that the estimates of $\kappa_n$ and $\sigma_n$ are defined by the profiles of the amplitude spectra that are invariant to the time shifts of the time function under the analysis. This provides means to use the value of the segmentation point $\chi_{n-1}$ as a provisional estimate (during the stages of the $\kappa_n$ and $\sigma_n$ estimation) of the parameter $\tau_n$. Accordingly, Equations (28) and (29) are presented for the purposes of the time to frequency transformations in the following forms:

$$\gamma_1(t) \cong u(t) \text{ for } 0 \le t \le \chi_1, \qquad (30)$$

$$\gamma_n(t) \cong u(t) - v_{n-1}(t) \text{ for } \chi_{n-1}-1 \le t \le \chi_n. \qquad (31)$$

To support the time to frequency domain transformations by standard procedures, the waveform element of Equation (31) is shifted by $\chi_{n-1}$ and described as a single function:

$$y_n(t) = u(t - \chi_{n-1}) - v_{n-1}(t - \chi_{n-1}), \qquad (32)$$

in the interval $[0, \lambda_n]$, where $\lambda_n = \chi_n - \chi_{n-1}$. This function is named an empirical component kernel (ECK).

In step 105 the ECK $y_n(t)$ is transformed from the time domain to the frequency domain using numerical estimation of the finite cosine and sine Fourier transformations. More particularly, the similar basis function (SBF) algorithm disclosed in Melkonian (2010) (see Melkonian D. "Similar basis function algorithm for numerical estimation of Fourier integrals". Numer Algor., 2010, vol. 54, pp. 73-100) is used, the contents of which is incorporated whereby by reference.

The SBF algorithm is an original version of Filon-type methods that provide a maximum precision in the numerical estimation of trigonometric integrals using polynomial interpolation. In contrast to conventional digital spectral analysis performed by the Fast Fourier Transform (FFT) and its modifications, the SBF algorithm is free of the necessity to deal with strict grids of computational points in both the time and frequency domains. The same is particularly advantageous in the present case where the lengths of the signal segments submitted to the time to frequency transformation in step 105 are variable. In the frequency domain, the chief advantage of the flexible choice of the computational points is the possibility to express the frequency domain dependencies using a logarithmic frequency scale.

Since the SBF algorithm is realized by universal procedures, the subscript "n" (number of the cycle in the recursion) is omitted in the following descriptions of the algorithm.

The SBF algorithm is addressed to the estimation of the following finite cosine and sine Fourier transformations:

$$Y_C(\omega) = \mathfrak{S}_C\{y(t), \lambda\} = \int_0^\lambda y(t)\cos(\omega t)dt, \qquad (33)$$

$$Y_S(\omega) = \Im_S\{y(t), \lambda\} = \int_0^\lambda y(t)\sin(\omega t)dt, \quad (34)$$

where $\omega=2\pi f$ is angular velocity, and f is frequency. Notations $\Im_C\{y(t),\lambda\}$ and $\Im_S\{y(t),\lambda\}$ used in these equations presume that $y(t)=0$ at $t \geq \lambda$. These are the real and imaginary parts of the complex spectrum of $y(t)$ $$Y(i\omega) = Y_C(\omega) - iY_S(\omega), \quad (35)$$

where $i=\sqrt{-1}$.

The corresponding amplitude spectrum is:

$$Y(\omega) = |Y(i\omega)| = \sqrt{Y_C^2(\omega) + Y_S^2(\omega)}. \quad (36)$$

The transcription of y(t) into a digital form specifies y(t) by its sampled values $y_i = y(t_i)$ in a finite number of nodal points $t_i$ (i=0, 1, ..., N) with $t_0=0$ and $t_N=\lambda$. The nodes need not be spaced equally. Thus, the calculations are addressed to the set of data points $\{(y_0, t_0), \ldots, (y_i, t_i), \ldots, (y_N, t_N)\}$. Using these data points, y(t) is interpolated over its samples by a piece-wise linear polynomial h(t). The interpolant must satisfy the following interpolation condition:

$$h_i = y_i \text{ for } i=0,1,\ldots,N, \quad (37)$$

where $h_i=h(t_i)$.

On assumption that $y_i=0$ for $i \geq N$, the SBF algorithm creates for the interval $[0, \lambda]$ the interpolant as the sum of similar basis functions:

$$h(t) = \sum_{i=0}^{N-1} a_i \theta_i(t), \quad (38)$$

where $a_i$ are the weighting coefficients, and $\theta_i(t)$ is a similar basis function (SBF). The SBF is defined by the similarity relationship:

$$\theta_i(t) = r(t/t_{i+1}). \quad (39)$$

This simple parametrized time scaling produces the family of SBFs from a basic finite element $$r(t) = \begin{cases} 1-t & \text{if } 0 \leq t \leq 1 \\ 0 & \text{otherwise} \end{cases} \quad (40)$$

termed a "triangular basis function" (TBF). The TBF is a unit right-angled triangle depicted in FIG. 9C.

Figure 9:
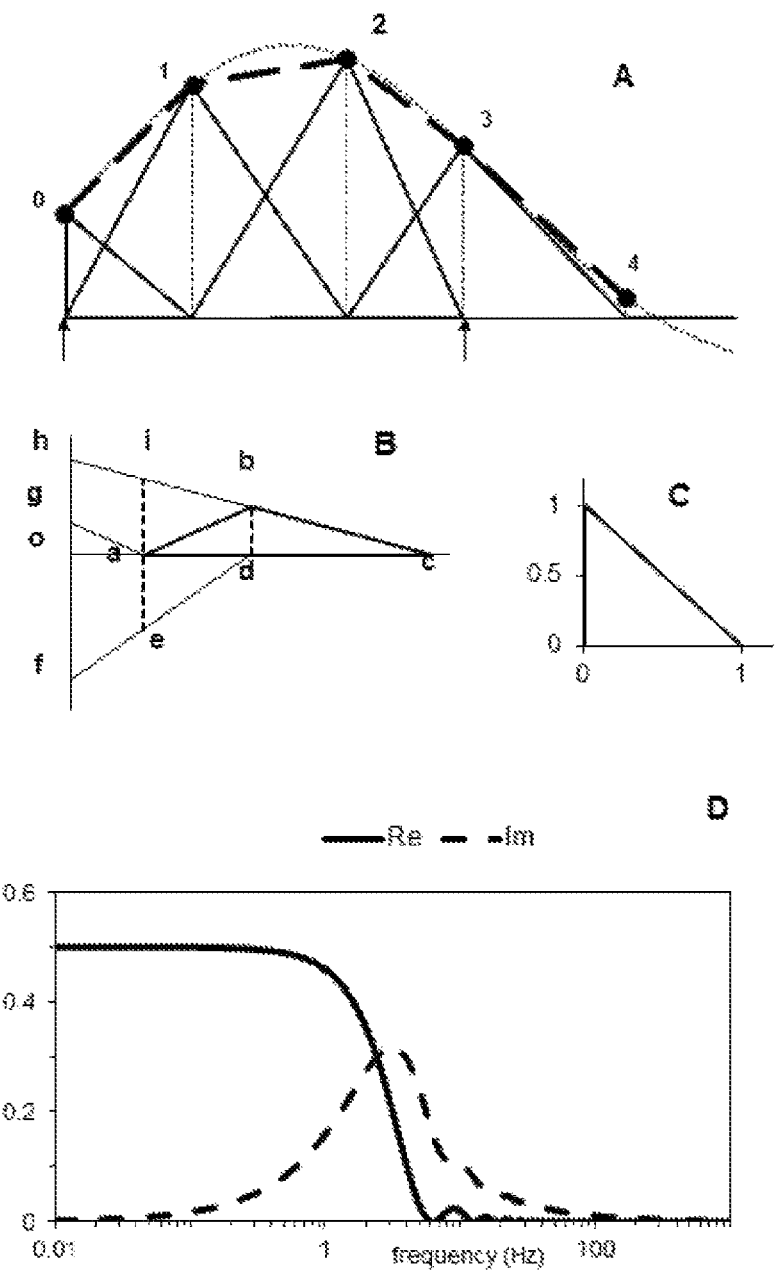
FIG. 9A exemplifies a decomposition of an interpolant into the sum of finite elements.
FIG. 9B shows the decomposition of a hat function into the sum of three triangular basis functions.
FIG. 9C shows a triangular basis function used in a similar basis function algorithm.
FIG. 9D shows the real and imaginary parts of the complex spectrum of the triangular basis function.

Using finite elements, the interpolant h(t) is presented in the form:

$$h(t) = h_0 \theta_0(t) + \sum_{i=1}^{N-1} h_i \varphi_i(t), \quad (41)$$

wherein $\varphi_i(t)$ is a hat function. The hat function $\varphi_i(t)$ is defined as:

$$\varphi_i(t) = \begin{cases} \dfrac{t - t_{i-1}}{t_i - t_{i-1}}, & \text{if } t_{i-1} \leq t < t_i \\ \dfrac{t_{i+1} - t}{t_{i+1} - t_i}, & \text{if } t_i \leq t < t_{i+1} \\ 0, & \text{otherwise} \end{cases} \quad (42)$$

on the mesh $t_0 < t_1 < \ldots < t_i < \ldots < t_N$. FIG. 9A exemplifies a decomposition of the interpolant h(t) as the sum of the TBF attached to the "0" sample followed by succession (samples 1, 2, 3, 4) of hat functions $\varphi_i(t)$ in the manner expressed in Equation (41).

Comparing Equations (37) and (41) shows that the hat functions of Equation (41) are replaced in Equation (37) by TBFs. The geometrical principles found useful in this connection is illustrated by FIG. 9B which shows the decomposition of the hat function (triangle abc) into the sum of three TBFs (triangles ohc, fod and goa). Application of this decomposition to all the hat functions in Equation (37) results in the following formula for the estimation of interpolation coefficients:

$$a_i = \alpha_i h_i - \beta_{i+1} h_{i+1} + \gamma_{i+2} h_{i+2}, 0 \leq i < N-3 \quad (43)$$
$$a_{N-2} = \alpha_{N-2} h_{N-2} - \beta_{N-1} h_{N-1},$$
$$a_{N-1} = \alpha_{N-1} h_{N-1},$$

where $$\alpha_i = \frac{t_{i+1}}{\Delta t_{i+1}} \quad (0 \leq i \leq N-1), \quad (44)$$

$$\beta_i = t_i \frac{\Delta t_{i+1} + \Delta t_i}{\Delta t_{i+1} \Delta t_i} \quad (1 \leq i \leq N-1),$$

$$\gamma_i = \frac{t_{i-1}}{\Delta t_i} \quad (2 \leq i \leq N-1),$$

$$\Delta t_i = t_i - t_{i-1}.$$

In the context of numerical solutions, the chief advantage of the construction of Equation (42) is that cosine and sine Fourier integrals from the TBF are expressed in an analytical form as $$R_C(\omega) = \Im_C\{r(t), 1\} = \int_0^1 r(t)\cos\omega t\, dt = \frac{1 - \cos\omega}{\omega^2}, \quad (45)$$

$$R_S(\omega) = \Im_S\{r(t), 1\} = \int_0^1 r(t)\sin\omega t\, dt = \frac{\omega - \sin\omega}{\omega^2}. \quad (46)$$

FIG. 9D shows these functions denoted as Re (Equation (45)) and Im (Equation (46)).

According to the theory of Fourier transforms (similarity theorem), the compression of the abscissa in the time domain corresponds to the expansion of the abscissa plus the contraction of the ordinate in the frequency domain. These operations establish the following similarity relationships between Fourier integrals of SBF and TBF:

$$\Im_C\{\theta_i(t), t_{i+1}\} = \int_0^{t_{i+1}} \theta_i(t)\cos\omega t\, dt = t_{i+1} R_C(t_{i+1}\omega), \quad (47)$$

$$\Im_S\{\theta_i(t), t_{i+1}\} = \int_0^{t_{i+1}} \theta_i(t)\sin\omega t\, dt = t_{i+1} R_S(t_{i+1}\omega). \quad (48)$$

Using these equations, the cosine and sine integrals from the interpolant of Equation (38) are expressed by the following analytical equations:

$$H_C(\omega) = \Im_C\{h(t)\} = \sum_{i=0}^{N-1} a_i t_{i+1} R_C(t_{i+1}\omega), \quad (49)$$

-continued $$H_S(\omega) = \mathcal{F}_S\{h(t)\} = \sum_{i=0}^{N-1} a_i t_{i+1} R_S(t_{i+1}\omega). \quad (50)$$

Since h(t) is an interpolant to y(t), these Fourier transforms are regarded as the estimates of the finite Fourier integrals of Equations (33) and (34). Consequently, $$Y_C(\omega) \approx H_C(\omega) \text{ and } Y_S(\omega) \approx H_S(\omega). \quad (51)$$

In this context, replacement of functions $R_C$ and $R_S$ in Equations (49) and (50) by their analytical expressions (45) and (46) leads to the following computational equations:

$$Y_C(\omega) \cong \sum_{i=0}^{N-1} a_i t_{i+1} \frac{1 - \cos(t_{i+1}\omega)}{(t_{i+1}\omega)^2}, \quad (52)$$

$$Y_S(\omega) \cong \sum_{i=0}^{N-1} a_i t_{i+1} \frac{\omega t_{i+1} - \sin(t_{i+1}\omega)}{(t_{i+1}\omega)^2}. \quad (53)$$

After estimation of the weighting coefficients from Equation (43), Equations (52) and (53) are directly applied to the data points.

The advantage of the SBF algorithm is that frequency characteristics can be computed at arbitrary sets of angular frequencies. The following procedures of parameter identification employ logarithmic frequency scale. Accordingly, the samples $Y_C(\omega_i)$ and $Y_S(\omega_i)$ of frequency characteristics are estimated at the points $$\omega_i = \omega_A C^i (i=0, \ldots, J), \quad (54)$$

where C>1 is a constant that defines the sampling rate on a logarithmic abscissa scale, and $\omega_A$ is the initial frequency.

Typical values of C that correspond to 10, 20, 50 and 100 samples per decade are 1.2589, 1.122, 1.0471 and 1.0233, respectively.

The amplitude spectrum is calculated at the same points as follows:

$$Y(\omega_i) = \sqrt{Y_C^2(\omega_i) + Y_S^2(\omega_i)} \quad (55)$$

Given nth cycle of recursion, the corresponding amplitude spectrum $Y_n(\omega)$ serves for identification of $\kappa_n$ (weight) and $\sigma_n$ (dispersion) parameters. For this purpose method 100 (FIG. 3) next proceeds to step 106.

On the condition that angular frequency $\omega_A$ is selected in such a way that $Y_n(\omega_A) \approx Y_n(0)$, the weight is defined as $$\kappa_n = Y_n(\omega_A). \quad (56)$$

Decisive in this regard are the tests of the adequacy of Gaussian amplitude spectrum of Equation (21) as a model of the empirical amplitude spectrum. The tests are applied to the normalized amplitude spectrum calculated from Equation (55), and use the estimate of parameter $\kappa_n$ from Equation (56):

$$\tilde{Y}_n(\omega_i) = Y_n(\omega_i)/\kappa_n. \quad (57)$$

Figure 10A:
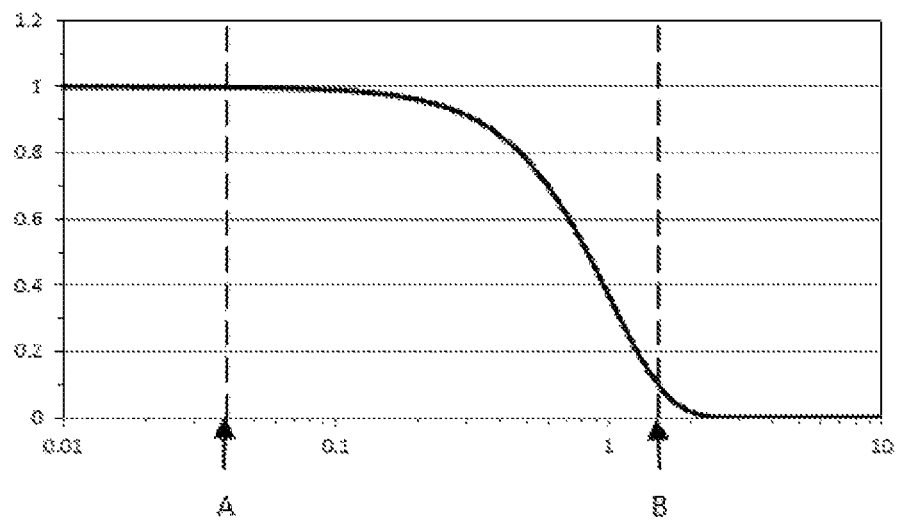
FIG. 10A illustrates the amplitude template used for estimation of a parameter $\sigma$.

Comparison of this spectrum with the model of Equation (21) is performed on a logarithmic frequency scale using the Gaussian spectrum as a template. The latter is defined analytically as $$T(v) = \exp(-v^2), \quad (58)$$

where v is real dimensionless variable. This function is shown in FIG. 10A. For numerical calculations, the template is defined by its sampled values at the points, $$v_m = v_A C^m (m=0, \ldots, M), \quad (59)$$

where C>1 is the same constant as in Equation (54), and M+1 is the number of template's samples.

Thus, the template extends over the segment $[v_A, v_B]$, where $v_B = v_A C^M$. The boundary points $v_A$ and $v_B$ are indicated in FIG. 10A by the arrows A and B.

The samples of the empirical normalized amplitude spectrum with which the template is compared correspond to the following points on the logarithmic angular frequency scale:

$$\omega_i = \omega_A C^i (i=0, \ldots, J). \quad (60)$$

The frequency range (from $\omega_A$ to $\omega_J = \omega_A C^J$) and the sampling rate are defined by I and C parameters. An adequate choice of these parameters provides means for a sufficiently accurate representation of the amplitude spectrum in a digital form. The frequency range of the amplitude spectrum must exceed the frequency range over which the template is defined. Accordingly, I>M.

Figure 10B:
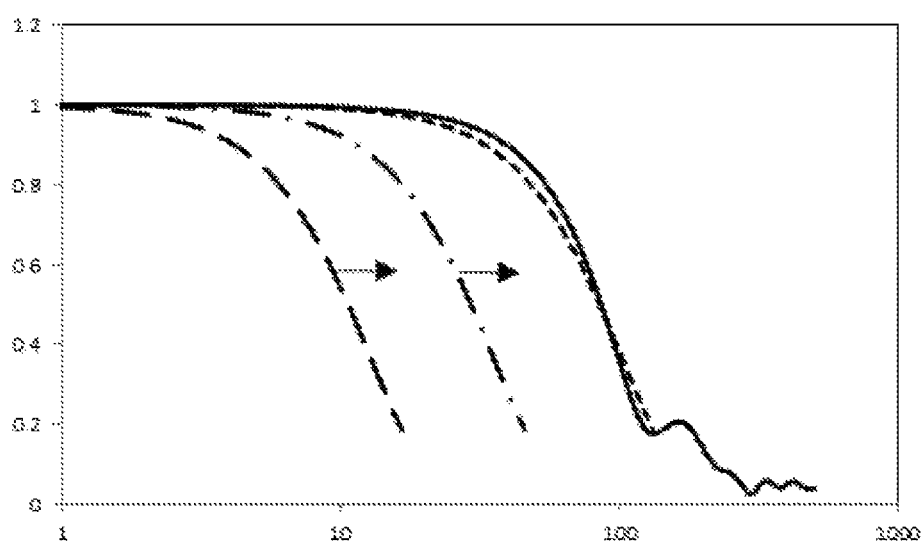
FIG. 10B exemplifies normalized empirical amplitude spectrum and different positions T1, T2 and T3 of the amplitude template during estimation of the parameter $\sigma$.

Template matching is performed by moving the Gaussian amplitude template throughout the abscissa scale. This is a step by step process during which the template samples remain unchanged while their locations on the abscissa scale are jointly shifted by multiplication the frequencies by the C constant. Thus, the first shift is performed by the change of the sequence of points of Equation (57) to the sequence of points $v_m = v_A C^{m+1}$ (m=0, 1, . . . , M). The sequence of the frequency points after the kth shift is $v_m = v_A C^{m+k}$ (m=0, 1, . . . , M). FIG. 10B exemplifies the empirical normalized amplitude spectrum $\tilde{H}_n(\omega)$ (solid black line) and Gaussian amplitude templates set at different shifts as the plots T1, T2 and T3.

The discrepancy between the template and empirical amplitude spectrum is evaluated at each template position using the mean squared error (MSE):

$$MSE(k) = \frac{1}{M} \sum_{m=0}^{M} \left[ \tilde{H}_n(\omega_0 C^{m+k-1}) - T(v_A C^m) \right]^2, \quad (61)$$

where k is the number of position (k=1, . . . , I−M+1).

In terms of the angular frequency, the initial position of the template covers the frequency range $[\omega_A, \omega_B]$ of the empirical spectrum, where $\omega_B = \omega_A C^M$. After k shifts the frequency range covered by the template is $[\Omega_A^k, \Omega_B^k]$, where $\Omega_A^k = \omega_A C^k$ and $\Omega_B^k = \Omega_B C^k$.

The best template match is indicated by the minimum value of the MSE. Given K as the number of the corresponding shift, the parameters $[\Omega_A^K, \Omega_B^K]$ define on the logarithmic angular frequency scale the template position at which the MSE is minimal. To decide whether this match substantiates the amplitude spectrum of Equation (21) as an adequate model of the empirical amplitude spectrum of Equation (55), the residual between these functions is regarded as a dimensionless error function $\varepsilon(\omega)$ defined by its samples $$\varepsilon(\omega_j) = \tilde{Y}_n(\omega_j) - T(v_A C^j), \quad (62)$$

where j has values from 0 to M, $\omega_j = \Omega_A^K C^j$.

Here, both $\tilde{Y}_n(\omega)$ and T(v) are dimensionless functions with equal initial values $\tilde{Y}_n(0) = T(0) = 1$. Accordingly, it is presumed that $\varepsilon(0) = 0$. The change of the error function with increase of the frequency is evaluated using the threshold value $\varepsilon_T$ in order to estimate the frequency range $[0, \omega_J]$ over which $$\varepsilon(\omega_j) \leq \varepsilon_T (j=0, \ldots, J), \quad (63)$$

The final value of $\tilde{Y}_n(\omega)$ at the boundary angular frequency $\omega_J$ is denoted as $\tilde{Y}_J = \tilde{Y}_n(\omega_J)$. This estimate is used to validate the quality of the template matching using categorization parameter $\xi$ that takes integer values from 1 to 5 according to the following schematic:

$\xi=1$ (grade E) if $0 \leq \tilde{Y}_J \leq 0.2$, $\xi=2$ (grade G) if $0.2 < \tilde{Y}_J \leq 0.4$, $\xi=3$ (grade S) if $0.4 < \tilde{Y}_J \leq 0.6$, $\xi=4$ (grade W) if $0.6 < \tilde{Y}_J \leq 0.8$, $\xi=5$ (grade U) if $\tilde{Y}_J > 0.8$. (64)

Given the grade, i.e. the value of $\xi$, the modelling result is qualified as follows: E—excellent, G—good, S—satisfactory, W—weak, U—unsuccessful.

Depending on the directive, in the case of W or U grade, the weight is neglected, i.e. $\kappa_n = 0$.

Figure 11A:
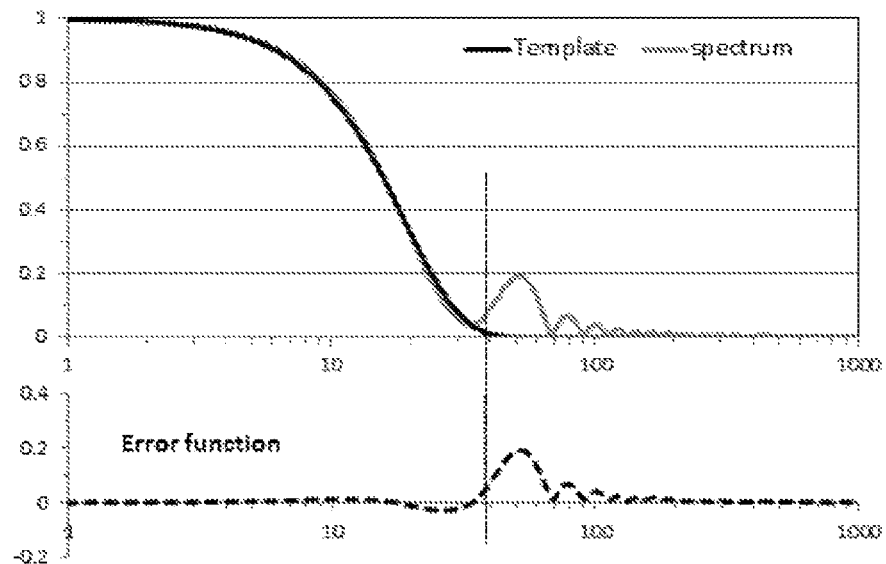
FIG. 11A illustrates the result of the template match to the normalized amplitude spectrum which belongs to a grade E.
Figure 11B:
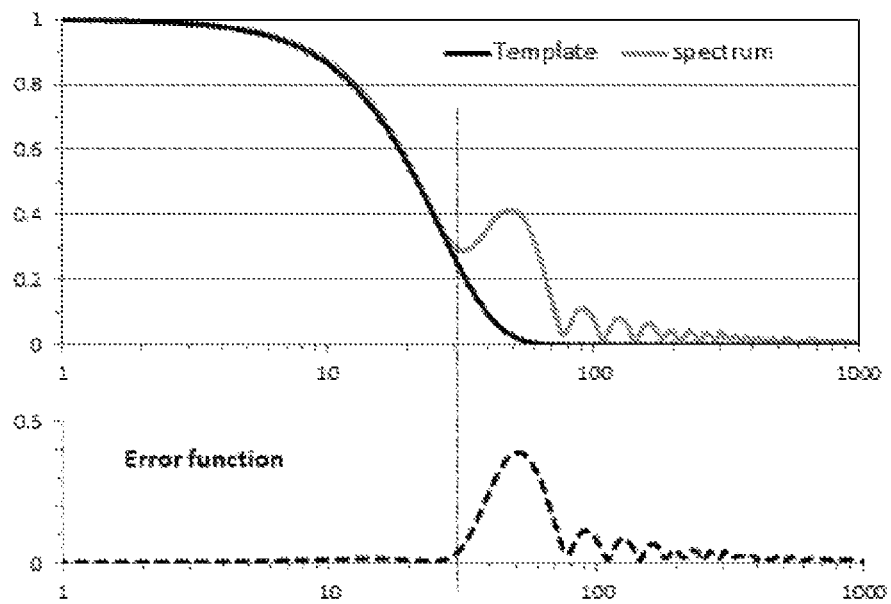
FIG. 11B illustrates the result of the template match to the normalized amplitude spectrum which belongs to a grade G.

FIGS. 11A and 11B illustrate the error functions for two examples of template matches using the threshold $\varepsilon_T = 0.05$. The corresponding boundary frequencies are indicated in FIG. 11A and FIG. 11B by the vertical dotted lines. These lines cross the amplitude spectra in FIG. 11A and FIG. 11B at the values 0.065 and 0.301, respectively. Consequently, the corresponding models belong to the classes E and G, respectively.

The best match defines some fixed position of the template at which the template samples may be associated with physical entities—the values of the angular frequency at the corresponding samples of $\tilde{Y}_n(\omega_j)$ on the logarithmic abscissa scale. In this context, the template samples are expressed as functions of the angular frequency in the following form $$T_F(\omega_m) = \exp\left[-\frac{(\sigma_n \omega_n)^2}{2}\right], (m = 0, 1, \ldots, M) \quad (65)$$

where subscript "F" indicates the final position of the template, $\sigma_n$ on denotes the $\sigma$ parameter from Equation (21) at the nth cycle of recursion.

Given arbitrary $\omega_m$, the required parameter $\sigma_n$ is calculated as $$\sigma_n = \sqrt{-\frac{2\ln T_F(\omega_m)}{\omega_m^2}}. \quad (66)$$

For stable accuracy of calculations, the angular frequency $\omega_m$ is selected from the range of frequencies over which $T_F(\omega_m)$ takes values from 0.4 to 0.8.

FIG. 12 exemplifies typical results of template matching. The middle panel shows a piece of EEG with the segmentation points indicated by the vertical dotted lines. The amplitude spectra of 6 consecutive EEG fragments taken between the segmentation points are shown by the solid lines in the upper and lower panels. The corresponding templates are depicted by the grey lines. Each example of the template match is supplemented by the following information: the grade of the model (E or B), the angular frequency $\Omega_B^K$, and the value $\tilde{Y}_n(\Omega_B^K)$.

Figure 13A:
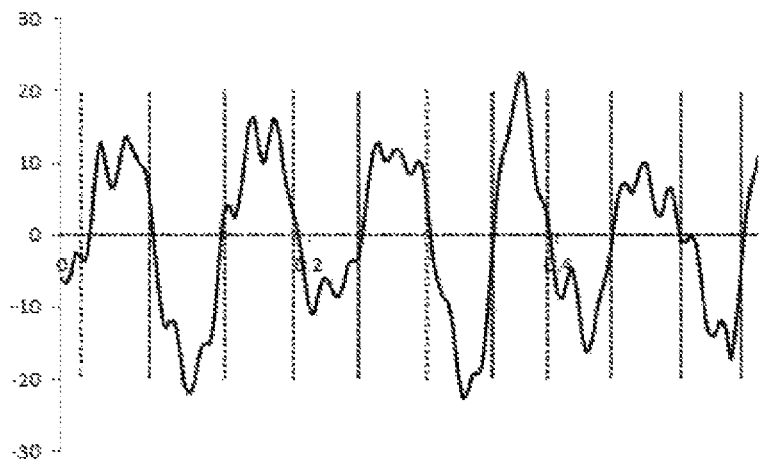
FIG. 13A shows an example EEG segmentation using low temporal resolution.
Figure 13B:
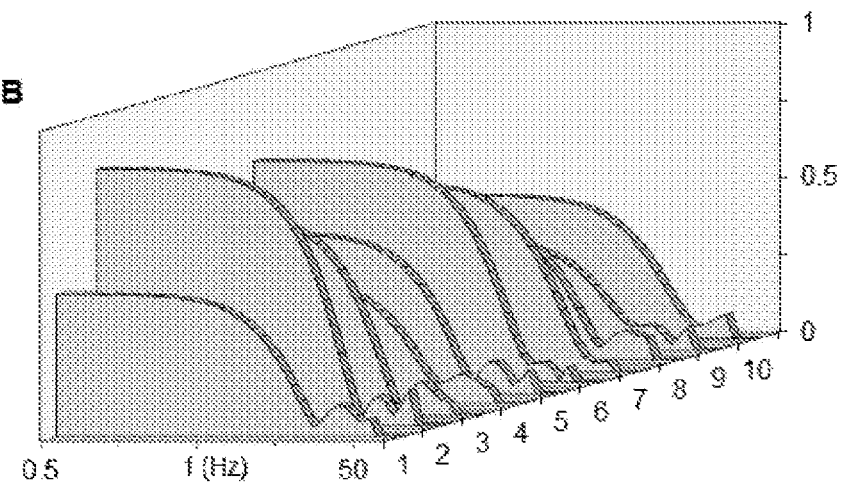
FIG. 13B shows the amplitude spectra of the 10 segments shown in FIG. 13A.
Figure 13C:
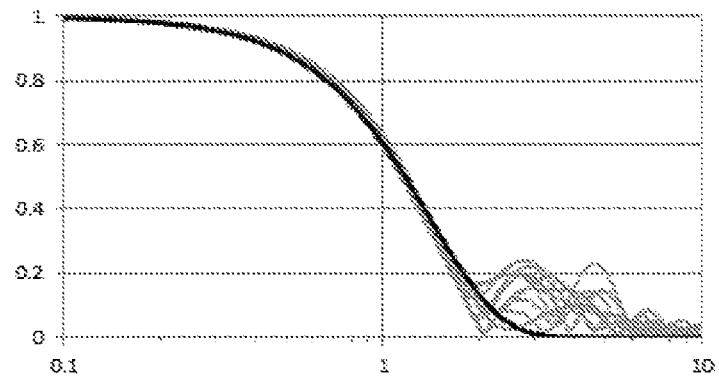
FIG. 13C shows the superposition of the amplitude spectra from FIG. 13B after normalization of both amplitude and frequency.

For the same signal redrawn in FIG. 13A, the amplitude spectra of the signal fragments between the segmentation points are shown in FIG. 13B. FIG. 13C shows superposition of these spectral characteristics after normalization of both amplitude and frequency. These plots are typical in the sense that the agreement with the Gaussian amplitude template (black line) is excellent for low and intermediate frequency ranges. Computer simulations have shown that the high frequency deviations are produced by irrelevant activities mixed with the functional components.

Referring again to method 100 (FIG. 3), following step 106 the method 100 proceeds to step 107 where the onset time $\tau_n$ is estimated. This procedure uses the normalized amplitude spectrum $\tilde{Y}_n(\omega)$ and the corresponding imaginary part of the complex spectrum after its normalization in a manner similar to the normalization of the amplitude spectrum using Equation (55):

$$\tilde{Y}_{Sn}(\omega_i) = Y_{Sn}(\omega_i)/\kappa_n, \quad (67)$$

where subscript n in the number of the cycle of recursion.

Figure 14A:
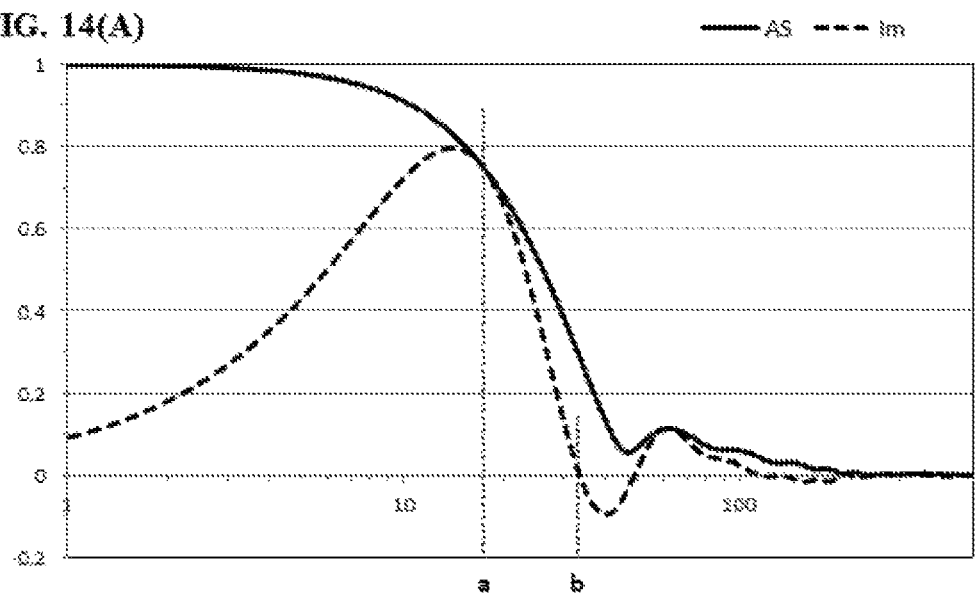
FIG. 14A shows the points a and b on the abscissa frequency scale on the basis of which the estimates of a parameter $\tau$ are obtained.
Figure 14B:
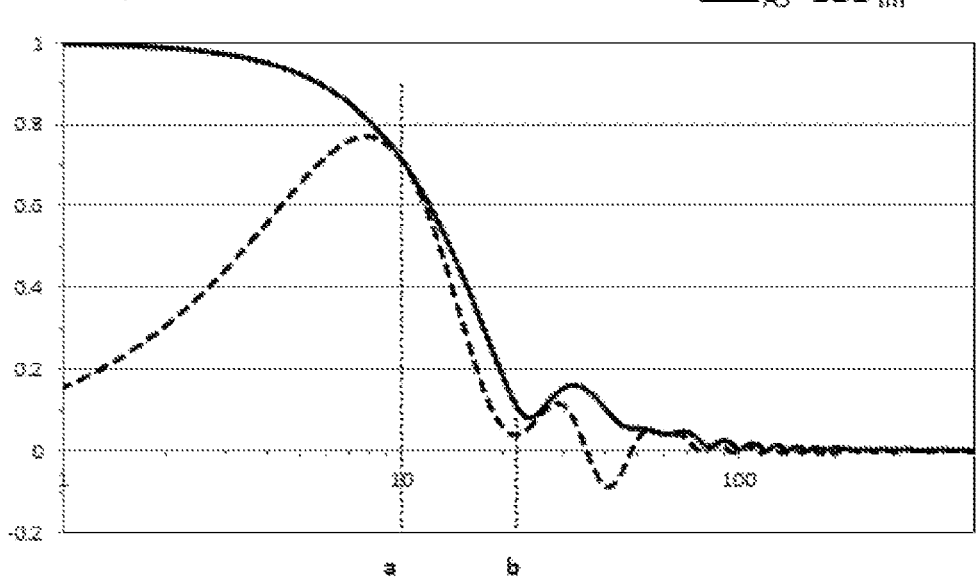
FIG. 14B exemplifies a situation when the point b on the abscissa scale is defined by the minimum of the imaginary part of the complex spectrum.

FIGS. 14A and 14B exemplify a typical form of these functions denoted AS (normalized amplitude spectrum $\tilde{Y}_n(\omega)$) and Im (normalized imaginary part of the complex spectrum $\tilde{Y}_{Sn}(i\omega)$). The general relationship between these functions includes the phase spectrum $\psi(\omega)$ in terms of which $$\tilde{Y}_{Sn}(\omega) = \tilde{Y}_n(\omega) \cdot \sin[\psi_n(\omega)]. \quad (68)$$

Similarly to the phase spectrum of Equation (22), $\psi_n(\omega)$ is expressed as linear dependency on the angular frequency in the form $$\psi_n(\omega) = \beta_n \omega. \quad (69)$$

The difference between the phase spectra of Equations (22) and (69) is accounted for by the shift coefficient $$s_n = \beta_n - \varepsilon \sigma. \quad (70)$$

Physically, this shift indicates the difference between the component onset time $\tau_n$ and the value of the segmentation point $\chi_{n-1}$. In this context, $$s_n = \tau_n - \chi_n. \quad (71)$$

Procedures of the SBF algorithm at the previous cycles of recursion take the segmentation point as a substitute of unknown onset time of the ECK under the analysis. Accordingly, the segmentation point serves as the time instant from which the numerical integration starts. This assumption has insignificant effect on the values of previously defined parameters because the amplitude spectrum, the source of $\kappa_n$ and $\sigma_n$ parameters, is invariant to the time shifts of the counterpart time function.

The $\tau_n$ estimation refers to the Equation (71) from which it follows that $$\tau_n = \beta_n - \varepsilon \sigma_n - \chi_n. \quad (72)$$

To use this equation, the unknown parameter $\beta_n$ should be estimated. Reference to the equations (68) and (69) indicates that parameter $\beta_n$ is fully defined by the following relationship between functions $\tilde{Y}_{Sn}(\omega)$ and $\tilde{Y}_n(\omega)$ as:

$$\beta_n = \frac{1}{\omega}\arcsin[\tilde{Y}_{Sn}(\omega)/\tilde{Y}_n(\omega)]. \quad (73)$$

To find parameter $\beta_n$ from this equation, it is sufficient to have estimates of $\tilde{Y}_{Sn}(\omega)$ and $\tilde{Y}_n(\omega)$ for a single point of angular frequency. However, to reduce computational errors, the two estimates are calculated at different angular frequencies $\omega_{1n}$ and $\omega_{2n}$. Given $\omega_{2n} > \omega_{1n}$, the choice of these frequencies presumes that in the interval from $\omega_{1n}$ to $\omega_{2n}$ $\tilde{Y}_{Sn}(\omega)$ decreases with increase of $\omega$.

Vertical dotted lines in FIGS. 14A and 14B indicated by the letter a on the abscissa scale, define angular frequency $\omega_{1n}$ as the point at which $\tilde{Y}_{Sn}(\omega_{1n})=\tilde{Y}_n(\omega_{1n})$. Reference to the Equation (73) shows that at this point $\beta_n=\pi/2\omega_{1n}$. Insertion of this value into Equation (72) provides the first estimate of the onset time:

$$\tau_n[1] = \frac{\pi}{2\omega_{1n}} - \varepsilon\sigma_n - \chi_n. \qquad (74)$$

According to the frequency domain models in the form of Equations (21) and (22), the expected form of $\tilde{Y}_{Sn}(\omega)$ is characterized by zero-crossing followed by local minimum as illustrated in FIG. 14A. Given such situation, the angular frequency $\omega_{2n}$ is defined as the point where $\tilde{Y}_{Sn}(\omega)$ crosses the abscissa scale, i.e. $\tilde{Y}_{Sn}(\omega_{2n})=0$.

In FIG. 14A $\omega_{2n}$ is indicated by the vertical dotted line originating from b on the abscissa scale. The value of the phase spectrum $\psi_n(\omega_{2n})=\pi$ defines $\beta_n=\pi/\omega_{2n}$.

Equation (72) gives the second estimate of the phase shift as $$\tau_n[2] = \frac{\pi}{\omega_{2n}} - \varepsilon\sigma_n - \chi_n. \qquad (75)$$

In some cases irrelevant elements of ECK distort expected frequency domain profile of $\tilde{Y}_{Sn}(\omega)$. The plot Im in FIG. 14B is a characteristic example of $\tilde{Y}_{Sn}(\omega)$ which reaches minimum instead of crossing the abscissa scale. The corresponding angular frequency is indicated by the vertical dotted line originating from b on the abscissa scale. This frequency replaces $\omega_{2n}$ in Equation (75) in order to obtain the second estimate of the onset time.

Given $\tau_n[1]$ and $\tau_n[2]$, the final choice of the onset time is based on the evaluation for different values of $\tau_n$ the discrepancies between $\tilde{Y}_{Sn}(\omega)$ and $W_S(\omega)$ from Equation (19) with $\sigma=\sigma_n$. The discrepancy is evaluated by the mean square error $$MSE = \frac{1}{N}\sum_{i=0}^{N}\left[\tilde{Y}_{Sn}(\omega_i) - W_S(\omega_i)\right]^2, \qquad (76)$$

where samples $\tilde{Y}_{Sn}(\omega_i)$ are computed using $\tau''[1]$ or $\tau_n[2]$ estimates of $\tau_n$, and N is integer selected in such a way that $\omega_N=\omega_{1n}$.

Given that MSE[1] and MSE[2] are relevant to $\tau_n[1]$ and $\tau_n[2]$, $\tau_n=\tau_n[1]$ if MSE[1]≤MSE[2]. Otherwise $\tau_n=\tau_n[2]$.

Thus, steps 106 and 107 estimate parameters $\langle\kappa_n, \sigma_n, \tau_n\rangle$ for the segment under consideration. Step 108 estimates the partial model $$V_n(t)=v_{n-1}(t)+\gamma_n(t) \qquad (77)$$

using Equation (26) before the method 100 then returns to step 104 from where steps 104 to 108 estimates the parameters $\langle\kappa_{n+1}, \sigma_{n+1}, \tau_{n+1}\rangle$ of the next segment.

FIG. 2B illustrates typical results of substituting each functional component shown in FIG. 2A (N100, p200, N200, P3a and P3b) with the QGK having parameters $\langle\kappa, \sigma, \tau\rangle$ that matches the corresponding ECK. The segments are denoted by the same symbols N100, P200, N200, P3a and P3b as their empirical counterparts in the FIG. 2A. FIG. 2C illustrates the sum of the component QGKs, i.e. a global model, as well as the original ERP signal shown in FIG. 2A for comparison. This is a satisfactory degree of agreement, since the parameters of the signal decomposition and identified components were derived entirely from general procedures of the inventive method, without any adjustments to make them fit the phenomena to which they were subsequently applied.

Figure 15A:
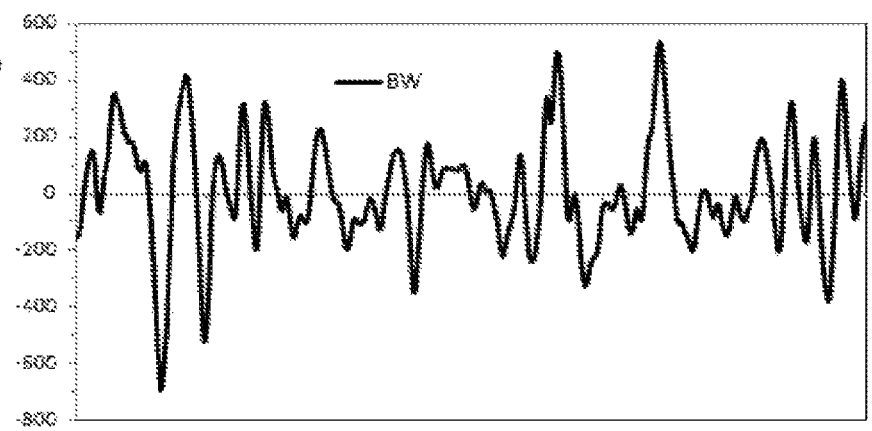
FIG. 15A shows an example of a breathing waveform of a speaking person.

More evidence in support of this conclusion has been obtained using non-stationary signals produced by different sources. To exemplify this point, FIG. 15A shows a 60 second segment of the breathing waveform of speaking person sampled at $\Delta=0.056$ s. The plot represents de-trended signal from breathing sensor using 5 passes for 3 and 47 point window filters. The y-axis units are the raw breathing sensor's outputs in bits.

Figure 15B:
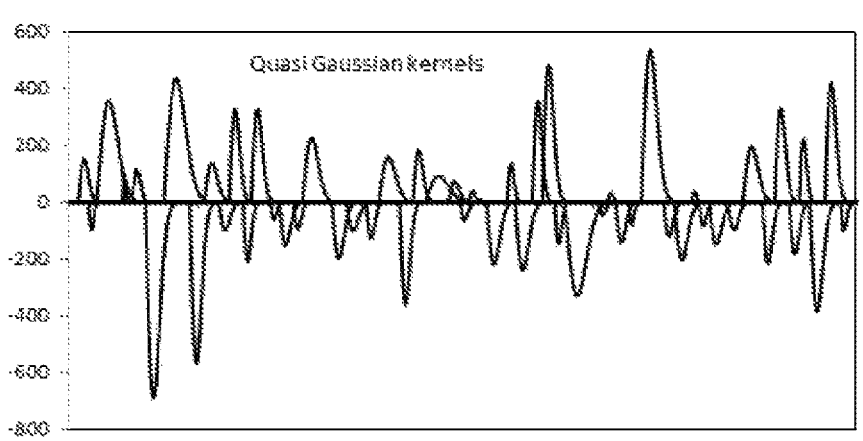
FIG. 15B shows the waveforms of 54 QGKs identified in the signal from FIG. 15A.
Figure 15C:
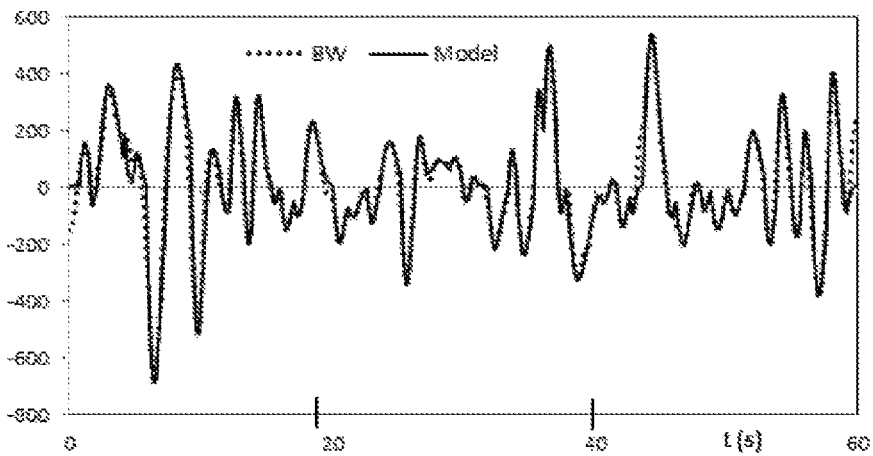
FIG. 15C shows the accuracy of the reproduction of the signal from FIG. 15A by the model synthesised as the sum of 54 identified QGKs.

FIG. 15B depicts superposition of 54 identified QGKs. A global model of the breathing waveform synthesized as the sum of all model components is shown in FIG. 15C by the solid line. At the same chart, the dotted line is the original breathing waveform reproduced from FIG. 15A.

Similarly to EEG, breathing waveforms are highly non-stationary signals. However, in contrast to the EEG produced by the sources of electricity (cortical neurons), the respiratory movements depend on a number of biomechanical factors governing the chest-wall motions. Thus, the physical processes underlying respiratory movements are quite different from the electrodynamics of the brain waves. Nevertheless, it appears that the method disclosed herein provides equally effective component identification tools for both applications. Remarkably accurate fits of QGKs to empirical waveforms are typical for a variety of electro-physiological signals (EEG, EMG, ECG) and breathing waveforms recorded from different species and under different experimental conditions. These results strongly support the chaos-based modeling (CBM) approach of the inventive methodology.

After all the segments are processed, and the parameters $\xi$, $\kappa$, $\sigma$, $\tau$ have been estimated for each of the segments formed in step 103, the method 100 continues to step 109 at which the modelling results are examined using parameter $\xi$ as marker. The value of parameter $\xi$ for each segment is compared with a defined threshold value $\xi_T$. If $\xi_n \geq \xi_T$, the model of the corresponding component is removed from the further processing stages. Typical values of $\xi_T$ are 4 and 5.

After removal of $N_1$ inappropriate components, the remaining components are renumbered in consecutive order from n=1 to $M=N_S-N_I$, where $N_S-1$ is the number of segmentation points. The set of the corresponding parameters is denoted by:

$$\mathfrak{R}_M=\{\xi,\kappa,\sigma,\tau\}, \qquad (78)$$

where $\xi=\{\xi_1, \ldots, \xi_i, \ldots, \xi_M\}$, $\kappa=\{\kappa_1, \ldots, \kappa_i, \ldots, \kappa_M\}$, $\sigma=\{\sigma_1, \ldots, \sigma_i, \ldots, \sigma_M\}$, $\tau=\{\tau_1, \ldots, \tau_i, \ldots, \tau_M\}$, are vectors each of which contains M values of the corresponding parameter.

The elements of the vectors $\kappa$ and $\sigma$ define the waveforms of model components while elements of the vector $\tau$ define a finite set of time points from which the developments of defined model components start. In this context, the vector $\kappa_\tau=\{\kappa,\tau\}$ provides the set of the data points $\{(\kappa_1, \tau_1), \ldots, (\kappa_i, \tau_i), \ldots, (\kappa_M, \tau_M)\}$, which represent the sequence of the values of the parameter $\kappa$ as the time series. Likewise, the vector $\sigma_\tau=\{\sigma,\tau\}$ provides the time series of the values of the parameter $\sigma$.

Time series are the standard form of numerical data to which numerous methods of signal processing are adapted. Thus, the disclosed method 100 that decomposes a signal into standard parameter sets provides means to apply to the non-stationary signal processing traditional methods of the time series analysis such as data standardization and transformation, principal component analysis, autocorrelation, autoregressive models, data-clustering, forecasting, etc.

Using the results of the decomposition of the non-stationary signal into the sets of component models (signal analysis), the method 100 offers a tool for solving an opposite problem, that being signal synthesis. This involves creating composites of components which are assigned to predefined classes.

Collection of the components for synthesis starts from the parameter classification procedure performed by step 110. The onset time is kept unchanged, and classification is applied to parameters $\xi$, $\kappa$ and $\sigma$ for each identified component model. More particularly, a parameter subset is determined from the whole set of model parameters $P_M$ according to the following conditions:

$$\xi_I \leq \xi_i \leq \xi_F$$

$$\kappa_I \leq \kappa_i \leq \kappa_F$$

$$\sigma_I \leq \sigma_i \leq \sigma_F \quad (79)$$

wherein $\xi_I$, $\kappa_I$, $\sigma_I$ and $\xi_F$, $\kappa_F$, $\sigma_F$ are constants that define the boundary (initial and final) values of the corresponding parameter.

From Equation (78), the parameter subset is denoted $$\hat{\mathfrak{R}}_L = \{\hat{\xi}, \hat{\kappa}, \hat{\sigma}, \hat{\tau}\} \quad (80)$$

where an overhat (^) denotes selected elements, and L is the number components. Obviously, L≤M.

Finally, method 100 ends in step 110 where the parameter subset $\hat{\mathfrak{R}}_L$ from step 110 is used for the synthesis of a partial model of the non-stationary signal in the form $$\hat{v}_L(t) = \frac{1}{\sqrt{2\pi}} \sum_{i=1}^{L} \frac{\hat{\kappa}_i}{\hat{\sigma}_i} \left[ \exp\left(-\frac{(t-\varepsilon\hat{\sigma})^2}{2\hat{\sigma}^2}\right) - \exp\left(-\frac{(t+\varepsilon\hat{\sigma})^2}{2\hat{\sigma}^2}\right) \right] \quad (81)$$

Classification and synthesis are multi-purpose procedures which can pursue different objectives. For example, exclusion of components with enormously small or large amplitudes can remove irrelevant elements of the signal. Selection of specific values of $\kappa$ and $\sigma$ can emphasise oscillatory components, etc.

The full set of model parameters $\mathfrak{R}_M$ and/or the set of selected parameters $\hat{\mathfrak{R}}_L$ may be stored on a storage medium of the computer system, or communicated to an external computer system, before further processing. The further processing may include different methods of model based signal processing such as optimal deconvolution, heuristic clustering algorithms, recursive Bayesian estimation, etc.

The foregoing describes only some embodiments of the present invention, and modifications and/or changes can be made thereto without departing from the scope and spirit of the invention, the embodiments being illustrative and not restrictive.

The claims defining the invention are as follows:

1. A computer implemented method of extracting functional components of a non-stationary biomedical signal selected from one or more of an electrocardiogram (ECG) signal, an electroencephalogram (EEG) signal and an electromyogram signal, with a Quasi-Gaussian Kernel as a basis element, thereby enabling improved detection and analysis of clinical and/or functional information contained therein, and for estimating parameters characterizing respective functional components, the method comprising the steps of:
   (a) applying multiple-pass moving average filters to estimate dynamic and baseline trends in a time course of the biomedical signal;
   (b) using the dynamic and baseline trends to construct a guide function indicative of signal fragments over which the functional components are developed;
   (c) adaptive segmenting of the guide function using zero-crossings and global and local minimums of a modulus of the guide function as segmentation points;
   (d) dividing the non-stationary biomedical signal into regions of component development, the non-stationary biomedical signal being segmented at points corresponding to the points of segmentation of the guide function;
   (e) compensating for overlap from Quasi-Gaussian Kernels matched to preceding functional components to form an Empirical Component Kernel, using the recursive sub-steps of:
      (i) transforming the Empirical Component Kernel to a frequency domain using a similar basis function algorithm;
      (ii) estimating weight and distribution parameters and validating parameter reliability in terms of predefined categorical grades by finding and assessing a best match between a normalized amplitude spectrum of the Empirical Component Kernel and the frequency domain template with a Gaussian profile; and
      (iii) estimating an onset time of the Quasi-Gaussian Kernel with the estimated weight and distribution parameters from an imaginary part of the Empirical Component Kernel complex spectrum by finding characteristic points that correspond to defined values of the phase spectrum;
   (f) on completion of the preceding cycles of recursion, expanding a model of the non-stationary biomedical signal composed from the sum of Quasi-Gaussian Kernels identified on the preceding cycles of recursion by adding the newly identified Quasi-Gaussian Kernel;
   (g) determining a categorization parameter ($\xi$) for each of the Quasi-Gaussian Kernels, wherein the categorization parameter for each Quasi-Gaussian Kernel is dependent upon an amplitude spectrum at a boundary angular frequency for the same Quasi-Gaussian Kernel;
   (h) removal of unfavorable Quasi-Gaussian Kernels using the categorization parameter ($\xi$) for assessment of identification results;
   (i) re-arranging the remaining identified components; and
   (j) creating a partial non-stationary signal model by selection of Quasi-Gaussian Kernel ensembles the parameters of which belong to the predefined categorical grades.

2. The method according to claim 1 wherein the categorization parameter ($\xi$) takes an integer value from 1 to 5; the categorization parameter is assigned according to a normalized amplitude spectrum at a boundary angular frequency as follows:

$\xi=1$ (grade E) if $0 \leq \tilde{Y}_j \leq 0.2$, $\xi=2$ (grade G) if $0.2 < \tilde{Y}_j \leq 0.4$, $\xi=3$ (grade S) if $0.4 < \tilde{Y}_j \leq 0.6$, ξ=4 (grade W) if $0.6 < \tilde{Y}_f \leq 0.8$, ξ=5 (grade U) if $\tilde{Y}_f > 0.8$, wherein a categorization parameter of 1 is defined as excellent (E), 2 is defined as good (G), 3 is defined as satisfactory (S), 4 is defined as weak (W), and 5 is defined as unsuccessful (U).

3. The method according to claim 1, wherein the dynamic trend is estimated by applying a low-pass infinite impulse response filter to the non-stationary biomedical signal.

4. The method according to claim 1, wherein the adaptive segmentation of the guide function uses zero-crossings only as the segmentation points.

5. The method according to claim 1, wherein an onset of each Quasi-Gaussian Kernel matched to respective Empirical Component Kernel coincides with the point of segmentation at an onset of the respective Empirical Component Kernel.

6. The method according to claim 5, wherein the estimating step further comprises the sub-step of estimating a revised onset of each Quasi-Gaussian Kernel matched to respective Empirical Component Kernel by finding a best match between the phase of the complex spectrum of the Empirical Component Kernel and the phase of the Gaussian complex spectrum.

7. An apparatus for extracting functional components of a non-stationary biomedical signal selected from one or more of an electrocardiogram (ECG) signal, an electroencephalogram (EEG) signal and an electromyogram signal, with a Quasi-Gaussian Kernel as a basis element, thereby enabling improved detection and analysis of clinical and/or functional information contained therein, and for estimating parameters characterizing respective functional components, the apparatus being adapted to:

apply multiple-pass moving average filters to estimate dynamic and baseline trends in a time course of the signal;

use the dynamic and baseline trends to construct a guide function indicative of signal fragments over which the functional components are developed;

adaptively segment the guide function using zero-crossings and global and local minimums of a modulus of the guide function as segmentation points;

divide the non-stationary biomedical signal into regions of component development, the non-stationary biomedical signal being segmented at points corresponding to the points of segmentation of the guide function;

compensate for overlap from Quasi-Gaussian Kernels matched to preceding functional components to form an Empirical Component Kernel, using the recursive sub-steps of:

(i) transform the Empirical Component Kernel to a frequency domain using a similar basis function algorithm;

(ii) estimate weight and distribution parameters and validating parameter reliability in terms of predefined categorical grades by finding and assessing a best match between a normalized amplitude spectrum of the Empirical Component Kernel and the frequency domain template with a Gaussian profile; and (iii) estimate an onset time of the Quasi-Gaussian Kernel with the estimated weight and distribution parameters from an imaginary part of the Empirical Component Kernel complex spectrum by finding characteristic points that correspond to defined values of the phase spectrum;

on completion of the preceding cycles of recursion, expand a model of the non-stationary biomedical signal composed from the sum of Quasi-Gaussian Kernels identified on the preceding cycles of recursion by adding the newly identified Quasi-Gaussian Kernel;

determining a categorization parameter (ξ) for each of the Quasi-Gaussian Kernels, wherein the categorization parameter for each Quasi-Gaussian Kernel is dependent upon an amplitude spectrum at a boundary angular frequency for the same Quasi-Gaussian Kernel;

removal of unfavorable Quasi-Gaussian Kernels using the categorization parameter for assessment of identification results;

rearrange the remaining identified components; and create a partial non-stationary biomedical signal model by selection of Quasi-Gaussian Kernel ensembles the parameters of which belong to the predefined categorical grades.

8. The method according to claim 3, wherein the adaptive segmentation of the guide function uses zero-crossings only as the segmentation points.

* * * * *